(12) United States Patent
Hanaya et al.

(10) Patent No.: US 9,790,033 B2
(45) Date of Patent: Oct. 17, 2017

(54) RACK TRANSPORTATION DEVICE

(71) Applicant: HITACHI, LTD., Tokyo (JP)

(72) Inventors: Tomonori Hanaya, Tokyo (JP);
Takahiro Yokoyama, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 15/318,222

(22) PCT Filed: Jun. 25, 2015

(86) PCT No.: PCT/JP2015/068413
§ 371 (c)(1),
(2) Date: Dec. 12, 2016

(87) PCT Pub. No.: WO2015/199200
PCT Pub. Date: Dec. 30, 2015

(65) Prior Publication Data
US 2017/0121120 A1    May 4, 2017

(30) Foreign Application Priority Data

Jun. 27, 2014   (JP) .................................. 2014-132154

(51) Int. Cl.
*B65G 37/00* (2006.01)
*B65G 15/10* (2006.01)
(Continued)

(52) U.S. Cl.
CPC ........... *B65G 37/00* (2013.01); *B65G 15/105* (2013.01); *B65G 25/08* (2013.01); *G01N 35/04* (2013.01);
(Continued)

(58) Field of Classification Search
CPC .... B65G 25/04; B65G 25/08; B65G 37/0005; B65G 43/10; G01N 2035/0415
(Continued)

(56) References Cited

U.S. PATENT DOCUMENTS 3,221,781 A * 12/1965 Forsstrom ................. B01L 9/06
141/130
3,236,321 A    2/1966 Katagir et al.
(Continued)

FOREIGN PATENT DOCUMENTS

JP    51-111382    10/1976
JP    59-105212    7/1984
(Continued)

OTHER PUBLICATIONS

English translation of International Preliminary Report on Patentability dated Jan. 5, 2017 in connection with PCT/JP2015/068413.
(Continued)

*Primary Examiner* — Joseph Dillon, Jr.
(74) *Attorney, Agent, or Firm* — Cooper & Dunham LLP

(57) ABSTRACT

A main drive mechanism provided with a main motor drives a rack on a first main path and a rack on a second main path simultaneously in the forward direction or simultaneously in the reverse direction. The rack is sent along a first auxiliary path by a first auxiliary drive mechanism. Then the rack is further sent in the forward direction along the second main path by the main drive mechanism. Once the rack leaves the first receiving region, the first claw member of the first auxiliary drive mechanism is sent to a retraction position and the rack is driven by the main drive mechanism in the reverse direction. The first claw member is then sent to an engagement position on the first main transportation path, the main drive mechanism is driven for transport in the forward direction, and the rack and the first claw member engage each other.

6 Claims, 13 Drawing Sheets

(51) Int. Cl.
*B65G 25/08* (2006.01)
*G01N 35/04* (2006.01)

(52) U.S. Cl.
CPC .............. *G01N 2035/046* (2013.01); *G01N 2035/0412* (2013.01)

(58) Field of Classification Search
USPC ....... 198/346.1, 346.2, 465.2, 574, 575, 794
See application file for complete search history.

(56) References Cited

U.S. PATENT DOCUMENTS

| | | | |
|---|---|---|---|
| 3,272,240 A | | 9/1966 | Roth |
| 3,809,208 A | * | 5/1974 | Shields .................. B65G 35/00 198/465.2 |
| 4,029,961 A | * | 6/1977 | Lohr ......................... G01T 7/08 198/346.2 |
| 4,040,533 A | | 8/1977 | De Boer et al. |
| 4,147,250 A | * | 4/1979 | Schulz .................. G01N 35/026 108/26 |
| 4,356,909 A | * | 11/1982 | November ............... G01N 1/18 198/465.2 |
| 4,488,633 A | * | 12/1984 | Kampf .................. G01N 35/026 198/341.01 |
| 4,506,777 A | * | 3/1985 | Kampf .................. G01N 35/026 198/341.02 |
| 4,573,851 A | * | 3/1986 | Butler ............... H01L 21/67313 206/832 |
| 4,710,122 A | * | 12/1987 | Villanueva ................ B28B 5/04 198/465.2 |
| 4,972,937 A | * | 11/1990 | Aarts ................... B23Q 7/1478 198/465.2 |
| 5,271,490 A | * | 12/1993 | Sticht .................... B23P 21/004 198/346.1 |
| 5,435,686 A | * | 7/1995 | Canner ................ C21D 9/0056 414/152 |
| 5,826,693 A | * | 10/1998 | Andersen ................ B65G 35/06 198/347.1 |
| 5,972,295 A | * | 10/1999 | Hanawa ........... G01N 35/00603 422/63 |
| 6,059,229 A | * | 5/2000 | Luria ..................... B65G 1/133 198/465.1 |
| 8,752,440 B2 | * | 6/2014 | Tatsutani ............ G01N 35/026 422/65 |
| 2007/0202011 A1 | * | 8/2007 | Nogawa ............... G01N 35/026 422/65 |
| 2007/0207056 A1 | * | 9/2007 | Veiner .................... G01N 35/04 422/63 |
| 2010/0093097 A1 | * | 4/2010 | Kawamura ...... G01N 35/00663 436/43 |
| 2010/0112703 A1 | * | 5/2010 | Tanaka ............. G01N 35/00603 436/47 |
| 2010/0248374 A1 | * | 9/2010 | Kitagawa ........... G01N 35/0092 436/47 |
| 2010/0282003 A1 | * | 11/2010 | Hamada ........... G01N 35/00722 73/863.91 |
| 2011/0290040 A1 | | 12/2011 | Tatsutani et al. |
| 2013/0195720 A1 | * | 8/2013 | Behnk ................... B65G 49/00 422/68.1 |

FOREIGN PATENT DOCUMENTS

| | | |
|---|---|---|
| JP | 63-6353 | 1/1988 |
| JP | 10-120167 | 5/1998 |
| JP | 2007-176665 | 7/2007 |
| JP | 2007-176666 | 7/2007 |
| JP | 2011-247778 | 12/2011 |

OTHER PUBLICATIONS

International Search Report in connection with PCT.JP2015/068413.

* cited by examiner

RACK TRANSPORTATION DEVICE

TECHNICAL FIELD

The present invention relates to a rack transporting device, the rack transporting device having two main transporting paths extending parallel to each other, for transporting a rack in a short-side direction of the rack, and an auxiliary transporting path intersecting with the two main transporting paths, for transporting the rack in a longitudinal direction of the rack. The rack transporting device transports the rack to one main transporting path, the auxiliary transporting path, and the other main transporting path in this order.

BACKGROUND

A rack transporting device is a device that transports a rack holding a plurality of containers. Each container contains a sample to be processed, such as a specimen and a reagent. Such a rack transporting device is integrated in a device such as a sample measurement device or a dispensing device. The sample measurement device is, for example, a device that performs radiation measurement on each sample. The dispensing device is a device that sucks each sample and dispenses it.

The rack transporting device transports a rack along preset transporting paths. The below-listed Patent Document 1 discloses a rack transporting device (10) provided with two main transporting paths (30, 32) for transporting a rack in the short-side direction of the rack and two auxiliary transporting paths (50, 52) for transporting the rack in the longitudinal direction of the rack. The two main transporting paths and the two auxiliary transporting paths are respectively arranged in parallel to each other, to thereby form a square as a whole. A rack (16) is transported on the main transporting path along the short-side direction of the rack and then transported on the auxiliary transporting path along the longitudinal direction. The rack circulates along the transporting paths formed into a square. In the main transporting path, a belt member (34) extends along the direction in which the main transporting path extends, and the belt member is driven to transport the rack.

The above-described reference numbers included in the parentheses are reference numbers used in the prior art document and do not relate to those used in embodiments of the present application.

CITATION LIST

Patent Literature

Patent Document 1: JP 2007-176666 A

SUMMARY

Technical Problem

The number of component parts of a rack transporting device is required to be reduced. If a drive mechanism for the two transporting paths (for example, the above-described main transporting paths of the prior art), such as, for example, a motor for driving the belt member can be shared, the requirement for reduction in the number of components can be met. However, if the motor is shared between the two transporting paths, and rack-transporting drive is performed on one transporting path, transporting drive is also performed on the other transporting path. Therefore, operations that reconcile transporting drive on the two transporting paths are required.

The object of the present invention is to provide a rack transporting device that reconciles transport-related operations on two transporting paths in the rack transporting device having a drive mechanism that simultaneously performs transporting drive on the two transporting paths.

Solution to Problem

The rack transporting device according to the present invention has a first main transporting path through which a rack is transported in a short-side direction of the rack, a second main transporting path which extends parallel to the first main transporting path and through which the rack is transported in the short-side direction of the rack, and a first auxiliary transporting path which extends in a direction orthogonal to the first main transporting path and the second main transporting path and connects between an end of the first main transporting path and an end of the second main transporting path, and through which the rack is transported in the longitudinal direction of the rack. The rack is transported from the first main transporting path to the second main transporting path through the first auxiliary transporting path. This transport direction will be referred to as a forward direction, and the direction opposite to the forward direction will be referred to as a reverse direction.

The rack transporting device has a main transporting drive mechanism that simultaneously drives and transports the rack on the first main transporting path and a rack on the second main transporting path in the forward direction or the reverse direction. The rack has a receiving hole formed in the side surface along its longitudinal direction. The rack transporting device further has a first auxiliary transporting drive mechanism that has a first claw member to be engaged with this receiving hole, and drives and transports the rack on the first auxiliary transporting path by feeding the first claw member.

The device has detectors for detecting positions of the rack. Specifically, there is provided a first end edge region arrival detector that detects that the rack arrives at a first end edge region, which is an end edge of the first main transporting path for transport in the forward direction. There is also provided a first receiving region arrival detector that detects that the rack arrives at a first receiving region on the second main transporting path, and the first receiving region receives the rack transported through the first auxiliary transporting path. There is further provided a first retraction detector that detects that the rack is retracted from the first receiving region.

In the above-described rack transporting device, first, the first auxiliary transporting drive mechanism drives and transports the rack from the first end edge region toward the first receiving region. When the first receiving region arrival detector detects arrival of the rack at the first receiving region, the main transporting drive mechanism drives and transports the rack in the forward direction. When the first retraction detector detects retraction of the rack from the first receiving region, the first auxiliary transporting drive mechanism moves the first claw member to a retraction position which does not interfere with the rack on the first main transporting path and the rack on the second main transporting path. After the first claw member is moved to the retraction position, the main transporting drive mechanism drives and transports the rack in the reverse direction. When the first receiving region arrival detector detects that the rack is returned and arrives at the first receiving region, the first auxiliary transporting drive mechanism moves the first claw member to a start edge position at which the first claw member can be engaged with a rack transported to the end edge region. After the first claw member is moved to the start edge position, the main transporting drive mechanism drives and transports the rack in the forward direction, thereby engaging the receiving hole of the rack with the first claw member. When the first end edge region arrival detector detects arrival of the rack at the first end edge region, the main transporting drive mechanism is stopped, and the first auxiliary transporting drive mechanism drives and transports the rack from the first end edge region to the first receiving region.

Another rack transporting device according to the present invention has a second auxiliary transporting path which extends in a direction orthogonal to the first main transporting path and the second main transporting path and connects between ends of the first main transporting path and the second main transporting path on the side opposite to the side where the first auxiliary transporting path is located, and through which the rack is transported in the longitudinal direction of the rack. The device further has a second auxiliary transporting drive mechanism for transporting a rack on the second auxiliary transporting path, and the second auxiliary transporting drive mechanism has a second claw member to be engaged with a receiving hole formed in a side surface of the rack along the longitudinal direction of the rack, and the second auxiliary transporting drive mechanism feeds the second claw member engaged with the receiving hole, thereby driving and transporting the rack on the second auxiliary transporting path. The device further has detectors relating to the second auxiliary transporting path. Specifically, there is provided a second end edge region arrival detector that detects that the rack arrives at a second end edge region, which is an end edge of the second main transporting path for transport in the forward direction. There is also provided a second receiving region arrival detector that detects that the rack arrives at a second receiving region on the first main transporting path, and the second receiving region receives the rack transported through the second auxiliary transporting path. There is further provided a second retraction detector that detects that the rack is retracted from the second receiving region. The rack is transported from the first main transporting path to the second main transporting path through the first auxiliary transporting path, and further from the second main transporting path to the first main transporting path through the second auxiliary transporting path. This transport direction will be referred to as a forward direction, and a direction opposite to the forward direction will be referred to as a reverse direction.

In the rack transporting device further having the second auxiliary transporting path, first, the first auxiliary transporting drive mechanism drives and transports the rack from the first end edge region to the first receiving region. When the first receiving region arrival detector detects arrival of the rack at the first receiving region, the main transporting drive mechanism drives and transports the rack in the forward direction. When the first end edge region arrival detector detects arrival of the rack at the first end edge region, the second auxiliary transporting drive mechanism drives and transports a rack from the second end edge region to the second receiving region. When the second receiving region arrival detector detects arrival of the rack at the second receiving region, the main transporting drive mechanism drives and transports the rack in the forward direction. When the first retraction detector detects retraction of the rack from the first receiving region, and when the second retraction detector detects retraction of the rack from the second receiving region, the first auxiliary transporting drive mechanism and the second auxiliary transporting drive mechanism respectively move the first claw member and the second claw member to retraction positions which do not interfere with the rack on the first main transporting path and the rack on the second main transporting path, respectively. After the first claw member and the second claw member are moved to the retraction positions, the main transporting drive mechanism drives and transports the racks in the reverse direction. When the first receiving region arrival detector detects that the rack is returned and arrives at the first receiving region, and when the second receiving region arrival detector detects that the rack is returned and arrives at the second receiving region, the first auxiliary transporting drive mechanism moves the first claw member to the start edge position at which the first claw member can be engaged with a rack transported to the first end edge region, and the second auxiliary transporting drive mechanism moves the second claw member to the start edge position at which the second claw member can be engaged with a rack transported to the second end edge region. After the first claw member and the second claw member are moved to the respective start edge positions, the main transporting drive mechanism drives and transports the racks in the forward direction, thereby engaging the receiving hole of the rack on the first main transporting path with the first claw member and engaging the receiving hole of the rack on the second main transporting path with the second claw member. When the first end edge region arrival detector detects arrival of the rack at the first end edge region, and when the second end edge region arrival detector detects arrival of the rack at the second end edge region, the main transporting drive mechanism is stopped, and the first auxiliary transporting drive mechanism drives and transports the rack from the first end edge region to the first receiving region.

A rack transporting device further having a second auxiliary transporting path can perform operations that differ from the above operation. First, the first auxiliary transporting drive mechanism drives and transports the rack from the first end edge region to the first receiving region. While the first auxiliary transporting drive mechanism performs transporting drive or when the first receiving region arrival detector detects arrival of the rack at the first receiving region, the second auxiliary transporting drive mechanism drives and transports a rack from the second end edge region to the second receiving region. When the first receiving region arrival detector detects arrival of the rack at the first receiving region and when the second receiving region arrival detector detects arrival of the rack at the second receiving region, the main transporting drive mechanism drives and transports the racks in the forward direction. When the first retraction detector detects retraction of the rack from the first receiving region, and when the second retraction detector detects retraction of the rack from the second receiving region, the first auxiliary transporting drive mechanism and the second auxiliary transporting drive mechanism respectively move the first claw member and the second claw member to the retraction positions which do not interfere with the rack on the first main transporting path and the rack on the second main transporting path, respectively. After the first claw member and the second claw member are moved to the retraction positions, the main transporting drive mechanism drives and transports the racks in the reverse direction. When the first receiving region arrival detector detects that the rack is returned and arrives at the first receiving region, and when the second receiving region arrival detector detects that the rack is returned and arrives at the second receiving region, the first auxiliary transporting drive mechanism moves the first claw member to the start edge position at which the first claw member can be engaged with a rack transported to the first end edge region, and the second auxiliary transporting drive mechanism moves the second claw member to the start edge position at which the second claw member can be engaged with a rack transported to the second end edge region. After the first claw member and the second claw member are moved to the respective start edge positions, the main transporting drive mechanism drives and transports the racks in the forward direction, thereby engaging the receiving hole of the rack on the first main transporting path with the first claw member, and engaging the receiving hole of the rack on the second main transporting path with the second claw member. When the first end edge region arrival detector detects arrival of the rack at the first end edge region, and when the second end edge region arrival detector detects arrival of the rack at the second end edge region, the main transporting drive mechanism is stopped, and the first auxiliary transporting drive mechanism drives and transports the rack from the first end edge region to the first receiving region.

Advantageous Effects of Invention

Transporting drive can be simultaneously performed on the first main transporting path and the second main path.

DESCRIPTION OF EMBODIMENTS

Figure 1:
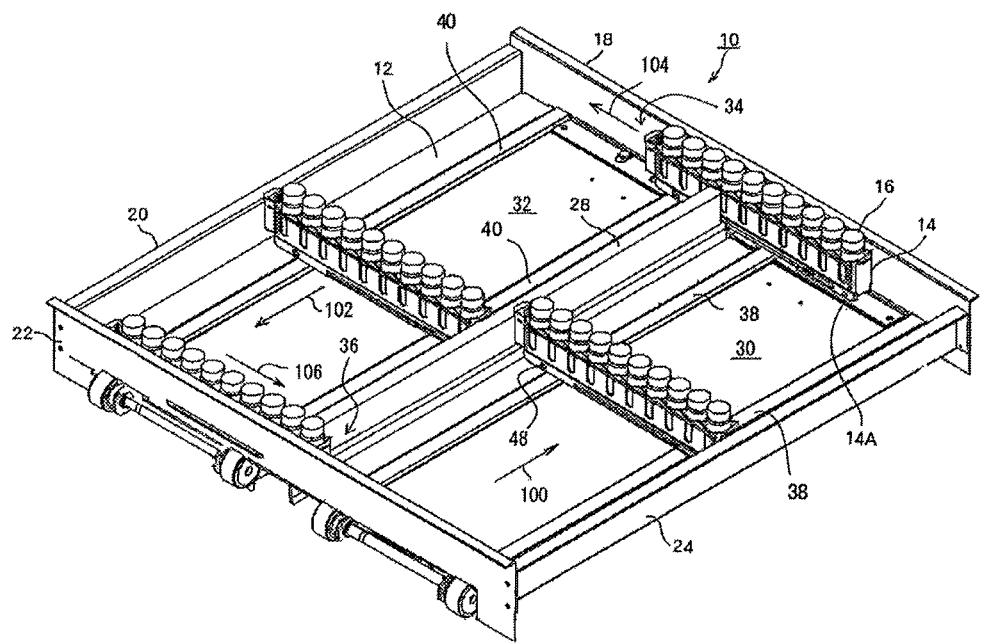
FIG. 1 shows a perspective view of an overview of a rack transporting device 10.

Preferred embodiments of the present invention will be described below with reference to the drawings. FIG. 1 shows a structure of the rack transporting device 10 according to the present embodiment, and particularly structures of transporting paths through which a rack 14 is transported. The rack transporting device 10 according to the present embodiment is also a device used in a sample measurement device that measures radiation dose emitted from samples. However, it may be used in other devices, such as a dispensing device.

The rack transporting device 10 has a transporting table 12 on which a plurality of racks are placed and on which the racks 14 are transported. The rack 14 holds containers 16 containing samples. The containers 16 are held such that ten containers 16 are arranged in a line in the rack 14. The number of holdable containers 16 may be other than ten, and the containers 16 may be arranged and held in two or more lines. The rack 14 is long in a direction along which the containers 16 are arranged, and this direction will be referred to as a "longitudinal direction." In addition, a direction that is orthogonal to the longitudinal direction will be referred to as a "short-side direction."

The transporting table 12 is surrounded by four sidewalls 18, 20, 22, and 24. In addition, a partition wall 28 is provided so as to bisect the transporting table 12. The partition wall 28 is provided so as to be parallel to the sidewalls 20 and 24, and there are provided spaces through which the rack 14 can pass between the ends of the partition wall 28 and the sidewalls 18 and 22, respectively. More specifically, there are provided spaces that are slightly larger than the size of the short-side direction of the rack 14 between the two ends of the partition wall 28 and the sidewalls 18 and 22 facing the respective ends. The partition wall 28 partitions the transporting table 12, to thereby form two transporting paths 30 and 32 that extend parallel to each other. The gaps between the partition wall 28 and the sidewalls 18 and 22 form transporting paths 34 and 36 that respectively connect between the ends of the two transporting paths 30 and 32. In order to distinguish between the transporting paths 30 and 32 and the transporting paths 34 and 36, the former and the latter are referred to as main transporting paths 30 and 32 and auxiliary transporting paths 34 and 36, respectively. In addition, in order to distinguish the main transporting paths 30 and 32 from each other, they are referred to as a first main transporting path 30 and a second main transporting path 32, respectively. In order to distinguish the auxiliary transporting paths 34 and 36 from each other, they are referred to as a first auxiliary transporting path 34 and a second auxiliary transporting path 36, respectively. A square transporting path for circulation is formed so as to have these four transporting paths 30, 32, 34, and 36 as its four sides.

Two transporting belts 38 are stretched across the first main transporting path 30 along the direction in which the first main transporting path 30 extends. In the first main transporting path 30, the rack 14 is placed on the two transporting belts 38 so as to bridge between these belts and is transported along the first main transporting path 30 by feeding the transporting belts 38. Two transporting belts 40 are stretched across the second main transporting path 32 along the direction in which the second main transporting path 32 extends. In the second main transporting path 32, the rack 14 is placed on the two transporting belts 40 so as to bridge between these belts and is transported along the second main transporting path 32 by the transporting belts 40. Although the rack 14 is moved on the transporting belts 38 and 40 as the transporting belts 38 and 40 are fed, when the rack 14 abuts against the sidewall or the rack which is located forward in the moving direction, the rack 14 slips on the transporting belts 38 and 40 and stays at that position. The transporting belts 38 and 40 are driven by a single motor (see FIG. 2). This motor will be referred to as a main motor 42. The main motor 42 may be an electric motor. Power transmission paths extending from the main motor 42 to the transporting belts 38 and 40 have no means for cutting off the transmission paths, such as a clutch. Therefore, when the main motor 42 is rotated, the transporting belts 38 and 40 are fed together. Here, feeding directions of the transporting belts 38 and 40 are directions that are opposite to each other. For example, the transporting belts 38 and 40 are respectively fed in the directions indicated by arrows 100 and 102 in FIG. 1. The main motor 42 can also be rotated in the reverse direction, and at this time, the transporting belts 38 and 40 are fed in the directions that are opposite to the arrows 100 and 102 in FIG. 1. As such, because the transporting belts 38 and 40 are driven by the single main motor 42, the rack 14 on the second main transporting path 32 is also moved when the rack 14 on the first main transporting path 30 is moved. The transporting belts 38 and 40 and the main motor 42 function as a main transporting drive mechanism that drives and transports the racks 14 on the main transporting paths 30 and 32.

Figure 2:
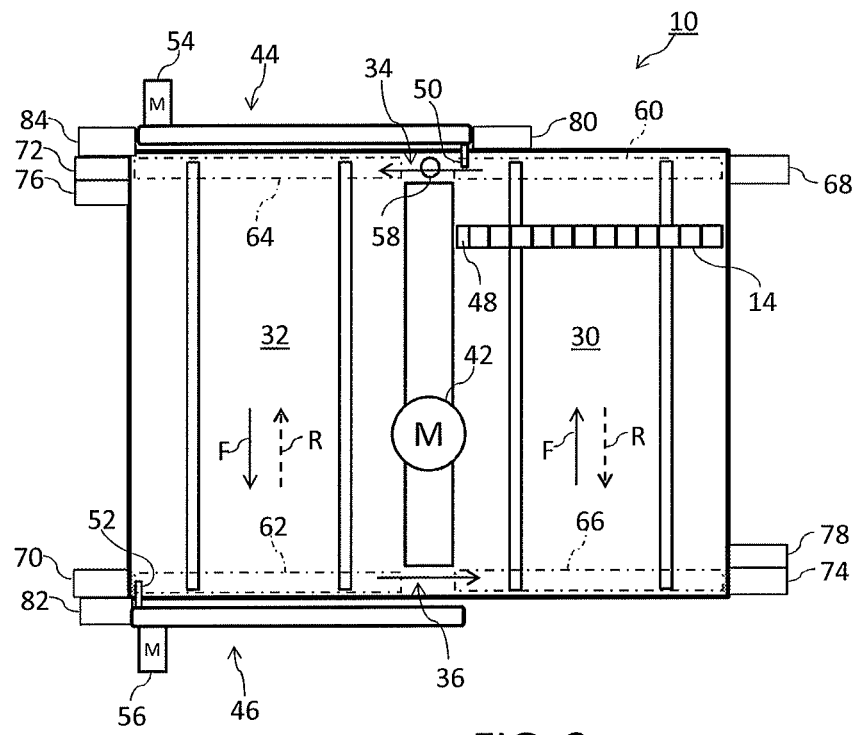
FIG. 2 shows a plane view of the overview of the rack transporting device 10.

Auxiliary transporting drive mechanisms 44 and 46 that drive and transport the racks 14 on the auxiliary transporting paths 34 and 36 are omitted in FIG. 1, but are shown in FIG. 2 in a simplified manner. The auxiliary transporting drive mechanisms 44 and 46 are respectively provided on the two auxiliary transporting paths 34 and 36 in a separate manner. When it is necessary to distinguish between the two auxiliary transporting drive mechanisms 44 and 46, one for driving the rack 14 on the first auxiliary transporting path 34 will be referred to as a first auxiliary transporting drive mechanism 44, and the other for driving the rack 14 on the second auxiliary transporting path 36 will be referred to as a second auxiliary transporting drive mechanism 46. Receiving holes 48 (see FIG. 1) are formed on side surfaces on both sides of the rack 14 along its longitudinal direction, particularly, in portions near the bottom of the rack 14. The first auxiliary transporting drive mechanism 44 includes a claw member 50 to be inserted into the receiving hole 48 and an electric motor that drives the claw member 50 via a belt. Similarly, the second auxiliary transporting drive mechanism 46 also includes a claw member 52 and an electric motor. These two motors are referred to as auxiliary motors 54 and 56, respectively. When it is necessary to distinguish between the two claw members and between the two auxiliary motors, they are respectively referred to as a first claw member 50, a second claw member 52, a first auxiliary motor 54, and a second auxiliary motor 56 so that they correspond to the auxiliary transporting drive mechanisms to which these claw members and auxiliary motors belong. The first auxiliary transporting drive mechanism 44 causes the first auxiliary motor 52 to move the first claw member 50 in the direction along the first auxiliary transporting path 34, with the first claw member 50 inserted into the receiving hole 48 of the rack. This enables the rack 14 to be driven and transported along the first auxiliary transporting path 34. The second auxiliary transporting drive mechanism 46 causes the second auxiliary motor 54 to move the second claw member 52 in the direction along the second auxiliary transporting path 36, with the second claw member 52 inserted into the receiving hole 48 of the rack. This enables the rack 14 to be driven and transported along the second auxiliary transporting path 36. The first auxiliary transporting drive mechanism 44 and the second auxiliary transporting drive mechanism 46 can also drive and transport the racks independently from each other. The first claw member 50 always protrudes to the first auxiliary transporting path 34 and is engaged with a rack 14 when the rack 14 is on the first auxiliary transporting path 34. Similarly, the second claw member always protrudes to the second auxiliary transporting path 36 and is engaged with a rack 14 when the rack 14 is on the second auxiliary transporting path 36.

The rack 14 circulates a circulation path formed by the four transporting paths 30, 32, 34, and 36 in the directions of the four arrows 100, 102, 104, and 106 shown in FIG. 1. More specifically, the rack 14 circulates so as to be fed from the first transporting path 30 to the second main transporting path 32 through the first auxiliary transporting path 34 and returned from the second main transporting path 32 to the first transporting path 30 through the second auxiliary transporting path 36. This direction will be referred to as a "forward direction." Although the rack 14 is usually transported in the forward direction, there are cases where it is transported in a "reverse direction" that is opposite to the forward direction.

FIG. 2 shows a simplified plane view of the rack transporting device 10. The first auxiliary transporting path 34 has a measurement section entrance 58 in a portion that faces the end of the partition wall 28. The container 16 held in the rack 14 is fed to a measurement section located under the transporting table 12 through this measurement section entrance 58. The container 16 subjected to the measurement is returned to the rack 14 through the measurement section entrance 58. For this purpose, the bottom of the rack 14 can be opened and closed, and a lift mechanism for moving the container 16 up and down between the rack 14 and the measurement section is also provided under the transporting table 12. Explanation of the details of the rack bottom and the lift mechanism will be omitted.

In FIG. 2, the forward direction for transporting the rack 14 is indicated by a solid line arrow F, and the reverse direction is indicated by a dotted line arrow R.

Hereinafter, specific regions on the transporting paths will be named for explanation. A region occupied by one rack 14 at the end edge of the first main transporting path 30 in the forward direction will be referred to as a "first end edge region 60." Further, a region occupied by one rack 14 at the end edge of the second main transporting path 32 in the forward direction will be referred to as a "second end edge region 62." A region on the second main transporting path 32, for receiving the rack 14 transported through the first auxiliary transporting path 34 will be referred to as a "first receiving region 64." A region on the first main transporting path 30, for receiving the rack 14 transported through the second auxiliary transporting path 36 will be referred to as a "second receiving region 66." Each of the first receiving region 64 and the second receiving region 66 is a region occupied by one rack 14.

The rack transporting device 10 has sensors for detecting the presence of the rack 14 in the above-described regions. For the first end edge region 60, a first end edge region arrival sensor 68 for detecting arrival of the rack 14 at the region is provided, and for the second end edge region 62, a second end edge region arrival sensor 70 for detecting arrival of the rack 14 at the region is provided. For the first receiving region 64, a first receiving region arrival sensor 72 for detecting arrival of the rack 14 at the region is provided, and for the second receiving region 66, a second receiving region arrival sensor 74 for detecting arrival of the rack 14 at the region is provided. Further, for the first receiving region 64, there is provided a first retraction sensor 76 for detecting that the rack 14 is transported through the second main transporting path 32 and retracted from the region. When the first receiving region arrival sensor 72 detects arrival of the rack 14, and then output signals of the first retraction sensor 76 have changed from those indicating "the presence of the rack" to those indicating "the absence of the rack," it becomes possible to detect that the rack 14 is retracted from the first receiving region 64. The second receiving region 66 also has a second retraction sensor 78 for detecting that the rack 14 is retracted from the region.

Proximity sensors such as optical sensors may be adopted as the above-described sensors, and sensors outputting ON signals when the rack 14 comes close to the sensors may be adopted. A control section (not shown) detects the presence and movement of the rack 14 based on values of output signals of these sensors. Therefore, combinations of the sensors with the control section function as detectors that detect arrival of the rack 14 at a target region and retraction of the rack 14 from the target region.

Positions and movements of the first claw member 50 and the second claw member 52 can be known based on rotation angles of the first auxiliary motor 54 and the second auxiliary motor 56. In particular, when the first and the second auxiliary motors 54 and 56 are stepping motors, rotation angles can be obtained from driving power pulses supplied to the motors, and therefore, positions and the like of the first and the second claw members 50 and 52 can be known by counting the number of pulses. This rack transporting device 10 has a sensor for directly detecting positions of the first and the second claw members 50 and 52 to enhance accuracy. When a position of the claw member obtained from a rotation angle of the motor is shifted from a position obtained from the sensor that directly detects a position of the claw member, the position obtained from the rotation angle is corrected using the directly detected position as a reference. The first auxiliary transporting drive mechanism 44 has sensors for detecting a position of the first claw member at both edges; that is, a start edge and an end edge, of a movable range of the first claw member 50. A first start edge position sensor 80 is a sensor that detects that the first claw member 50 is positioned at a start edge position at which the first claw member 50 can be engaged with a rack 14 transported through the first main transporting path 30. A first end edge position sensor 84 is provided for detecting that the first claw member 50 is positioned at an end edge position which is a position at which the first claw member 50 finishes transporting the rack 14 to the first receiving region 64. The second auxiliary transporting drive mechanism 46 has a second start edge position sensor 82 that detects that the second claw member 52 is positioned at a start edge position. The start edge position is a position at which the second claw member 52 can be engaged with a rack 14 transported through the second main transporting path 32.

A position of the first claw member 50 can be detected by the control section (not shown) based on outputs from the first start edge position sensor 80 and the first end edge position sensor 84 and a rotation angle of the motor. A position of the second claw member 52 can be detected by the control section (not shown) based on an output from the second start edge position sensor 82 and a rotation angle of the motor.

Figure 3:
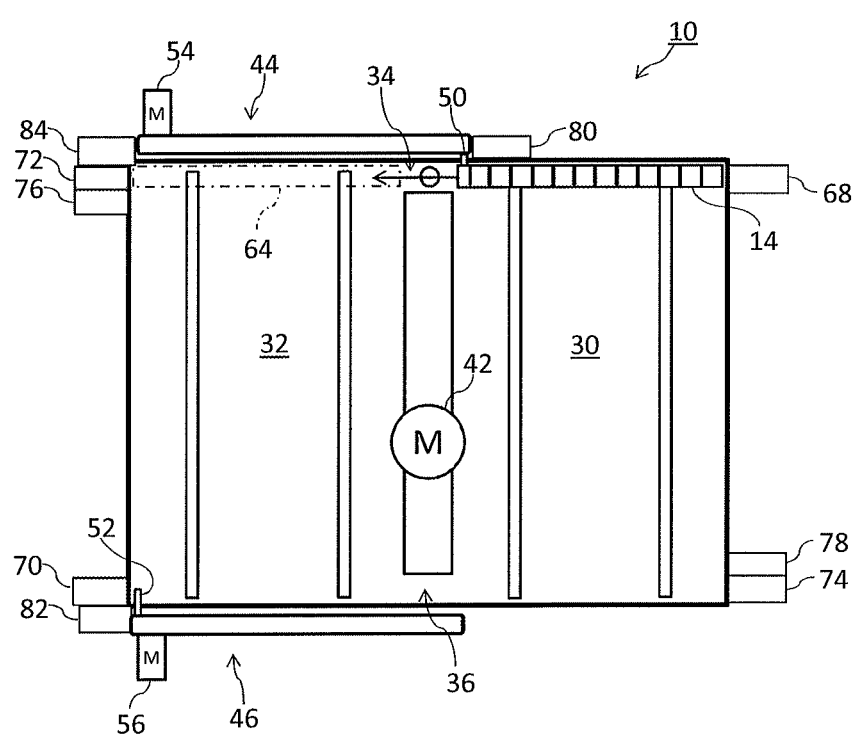
FIG. 3 shows an operation explanatory drawing of the rack transporting device 10 transporting one rack.

Next, operations of the rack transporting device 10 will be described with reference to FIGS. 3 to 14. FIGS. 3 to 14 are operation explanatory drawings of the case where one rack 14 circulates. The operations begin with the state shown in FIG. 3 where the rack 14 is placed in the first end edge region 60 of the first main transporting path 30. In order to obtain the state shown in FIG. 3, for example, the rack 14 is placed on the first main transporting path 30, and the main transporting drive mechanism is driven; that is, the main motor 42 is driven, to thereby drive and transport the rack 14 in the forward direction. When arrival of the rack 14 is detected by the first end edge region arrival sensor 68, the state shown in FIG. 3 is reached.

Figure 4:
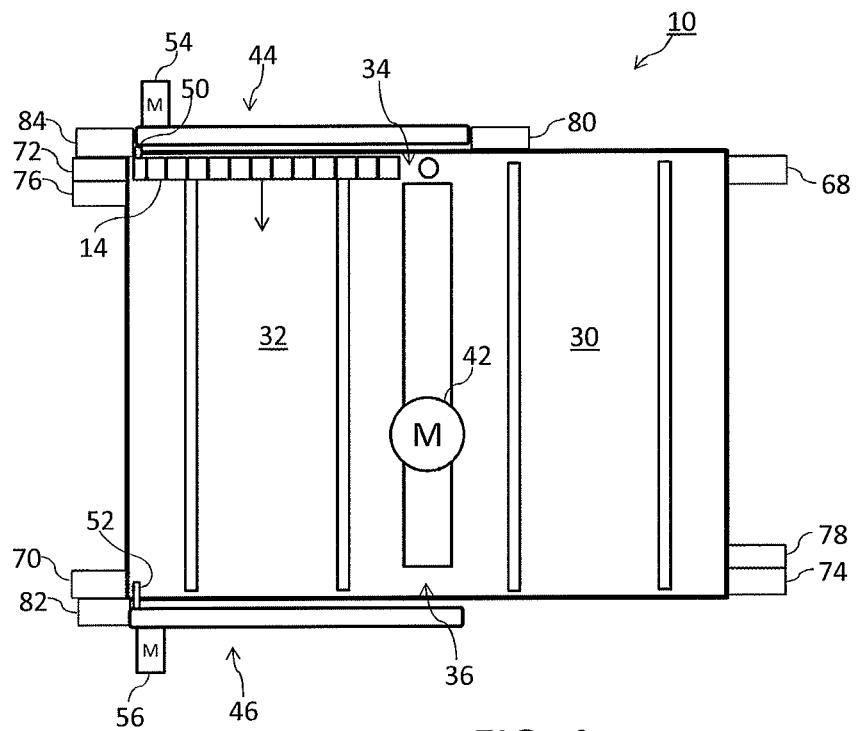
FIG. 4 shows an operation explanatory drawing of the rack transporting device 10 transporting one rack.

First, the first auxiliary transporting drive mechanism 44 drives and transports the rack 14 in the forward direction. When the rack 14 is transported, and the first container 16 reaches the position of the measurement section entrance 58, the rack 14 is stopped, and the container 16 is fed to the measurement section. After the measurement is finished, the container 16 is returned to its original position in the rack 14, and the rack 14 is transported until a next container 16 reaches the position of the measurement section entrance 58. This is repeated for each container 16, and after the measurement is finished for all of the containers 16 on this rack 14, the rack 14 is transported to the first receiving region 64 of the second main transporting path 32 (FIG. 4). Feeding of the rack 14 can be controlled based on a rotation angle of the first auxiliary motor 54.

Figure 5:
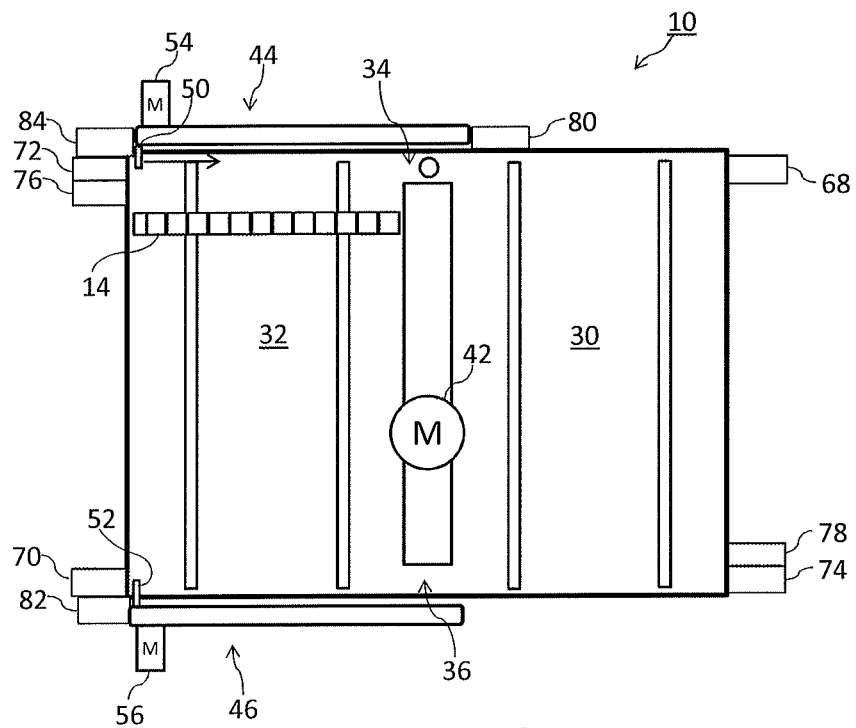
FIG. 5 shows an operation explanatory drawing of the rack transporting device 10 transporting one rack.
Figure 6:
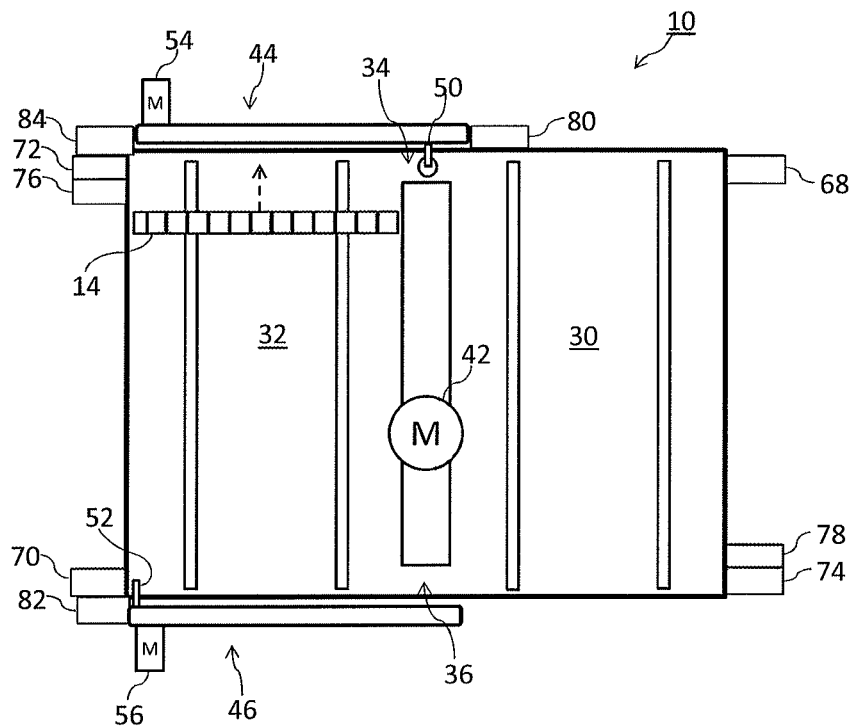
FIG. 6 shows an operation explanatory drawing of the rack transporting device 10 transporting one rack.
Figure 7:
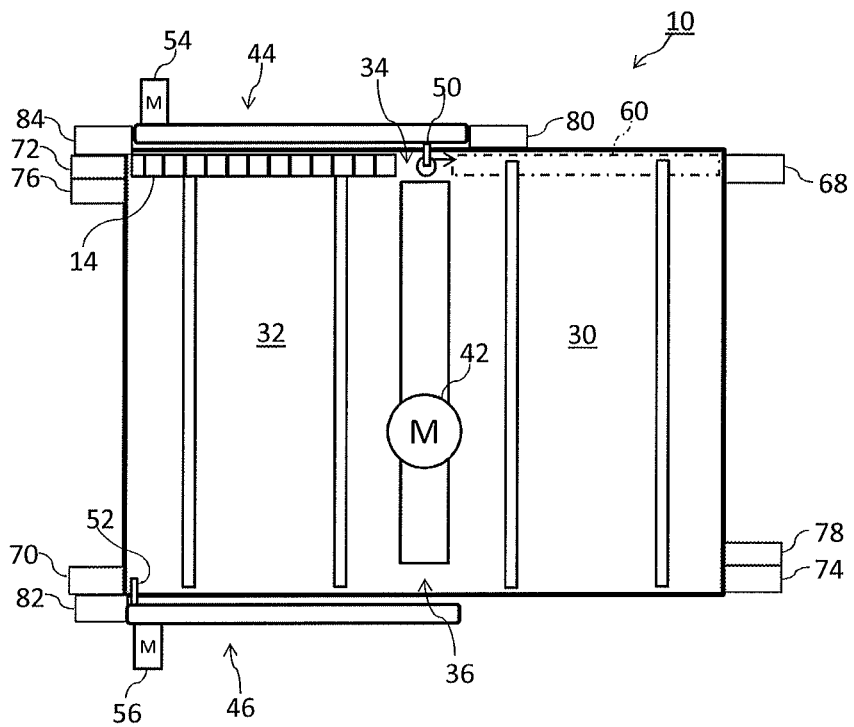
FIG. 7 shows an operation explanatory drawing of the rack transporting device 10 transporting one rack.

When it is confirmed that the rack 14 has arrived at the first receiving region 64 based on an output signal of the first receiving region arrival sensor 72, the main transporting drive mechanism drives the rack 14 in the forward direction. When the first receiving region arrival sensor 72 outputs an ON signal, and subsequently, the first retraction sensor 76 outputs an ON signal and then an OFF signal, it is detected that the rack 14 is retracted from the first receiving region 64 (FIG. 5). Retraction of the rack 14 from the first receiving region 64 allows the first claw member 50 to come out from the receiving hole 48 of the rack 14, thereby allowing release of engagement between them. When retraction of the rack 14 is detected, the main transporting drive mechanism is stopped, and the first claw member 50 is directed to the start edge and moved to a region sandwiched between the end of the partition wall 28 and the sidewall 18 (FIG. 6). This position is a position which does not interfere with the rack 14 on the first main transporting path 30 and the rack 14 on the second main transporting path 32, and hereinafter, this position will be referred to as a "retraction position." A position of the first claw member 50 can be known based on a rotation angle of the first auxiliary motor 54.

Next, the main transporting drive mechanism drives and transports the rack 14 in the reverse direction until the first receiving region arrival sensor 72 detects the rack 14 (FIG.

Figure 8:
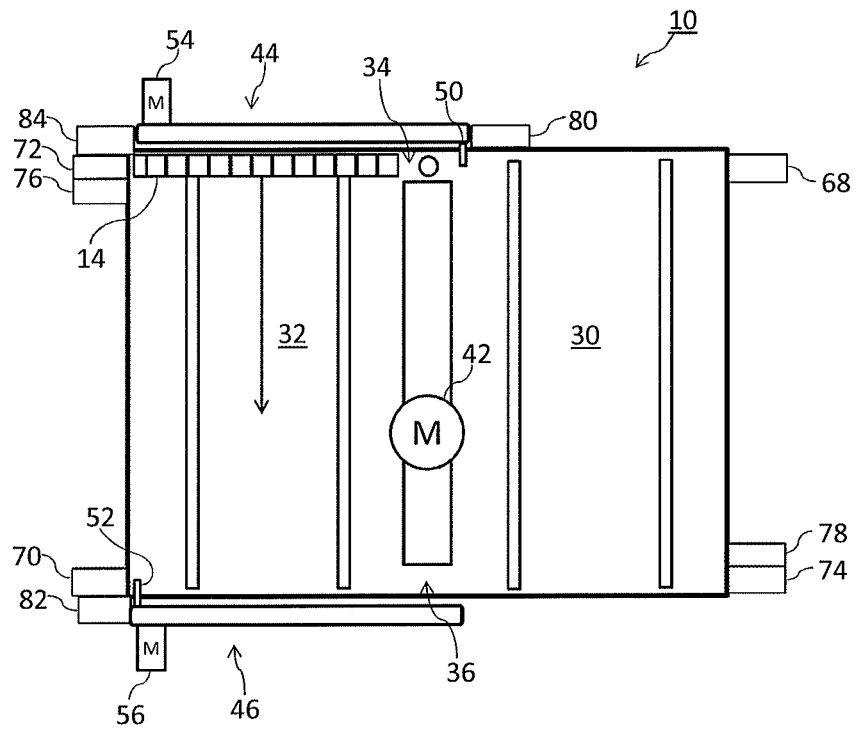
FIG. 8 shows an operation explanatory drawing of the rack transporting device 10 transporting one rack.

7). This operation by the main transporting drive mechanism also causes transporting drive to be performed on the first main transporting path 30 in the reverse direction, and this removes the rack 14 from the first end edge region 60. If the number of the racks 14 installed on the transporting table 12 is one, there is no possibility of the presence of the rack 14 in the first end edge region 60, but if a plurality of racks 14 are installed, there is a possibility of the presence of the rack 14 in the first end edge region 60. The first claw member 50 is moved to the start edge position, with no rack 14 positioned in the first end edge region 60 (FIG. 8). Arrival of the first claw member 50 at the start edge position can be detected by the first start edge position sensor 80. By removing the possibility of the presence of the rack 14 in the first end edge region 60 by transporting the rack 14 in the reverse direction by the main transporting drive mechanism, the first claw member 50 is prevented from interfering with the rack 14 when the first claw member 50 is returned to the start edge position.

Figure 9:
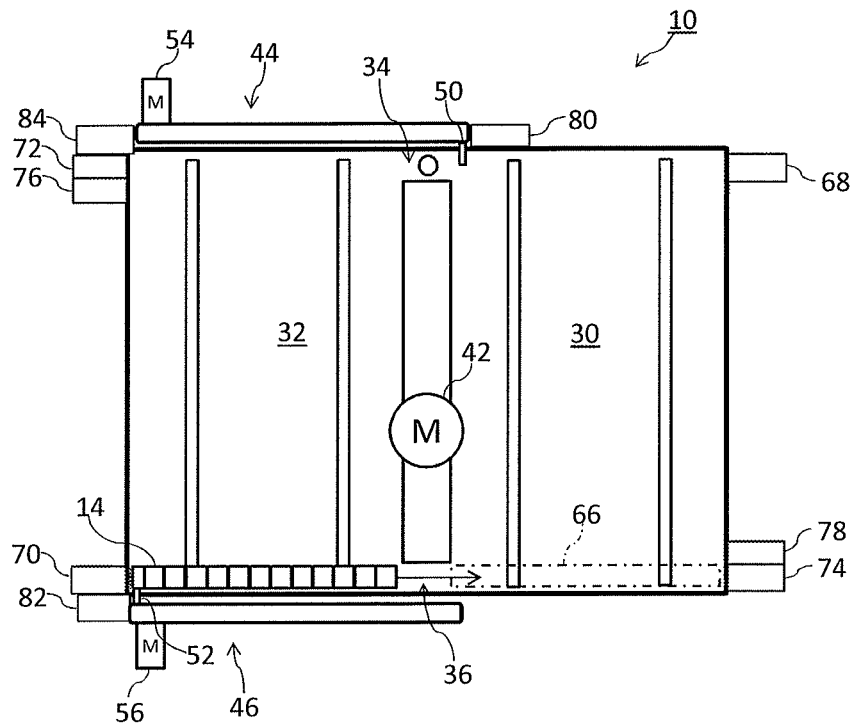
FIG. 9 shows an operation explanatory drawing of the rack transporting device 10 transporting one rack.
Figure 10:
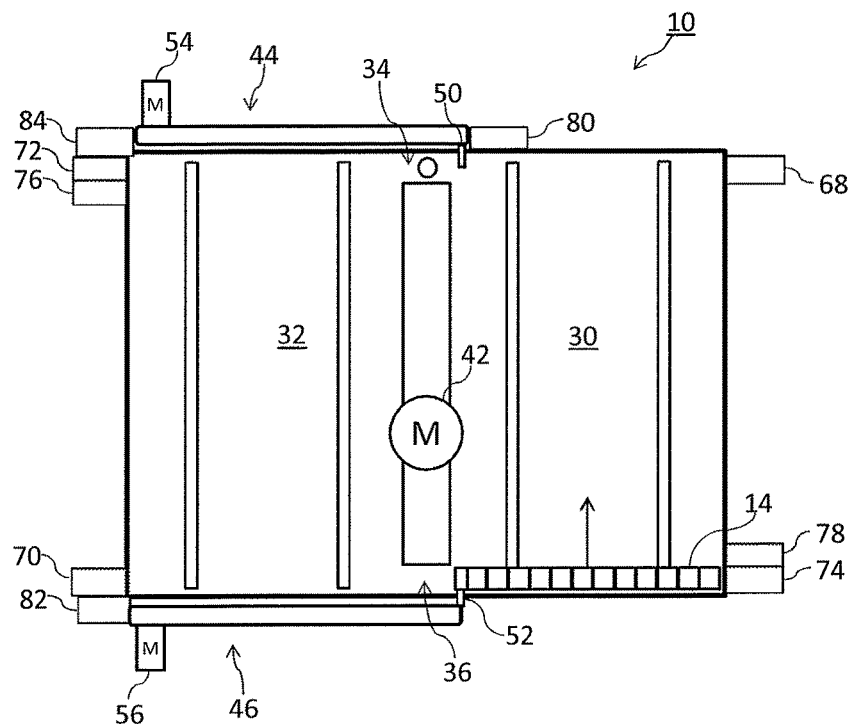
FIG. 10 shows an operation explanatory drawing of the rack transporting device 10 transporting one rack.
Figure 11:
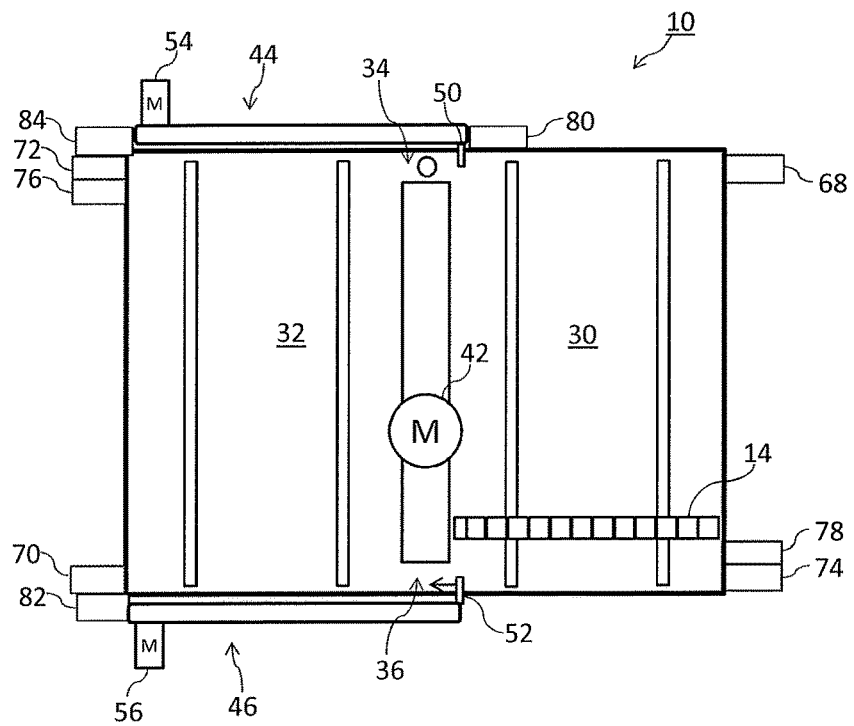
FIG. 11 shows an operation explanatory drawing of the rack transporting device 10 transporting one rack.
Figure 12:
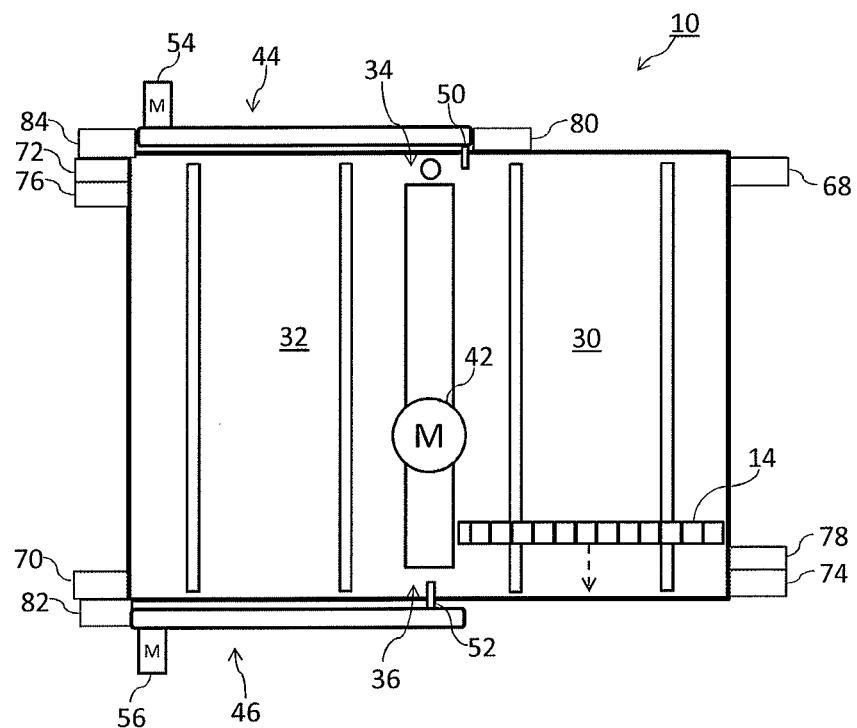
FIG. 12 shows an operation explanatory drawing of the rack transporting device 10 transporting one rack.

Next, the main transporting drive device drives and transports the rack 14 on the second main transporting path 32 in the forward direction until arrival of the rack 14 at the second end edge region 62 is detected based on an output signal of the second end edge region arrival sensor 70 (FIG. 9). Arrival of the rack 14 at the second end edge region 62 causes the second claw member 52 to be inserted into the receiving hole 48 of the rack, thereby allowing the rack 14 to be engaged with the second claw member 52. Further, because, at this time, transporting drive is also performed on the first main transporting path 30 in the forward direction, the rack 14 is removed from the second receiving region 66, even if it is on the first main transporting path 30. When the rack 14 arrives at the second end edge region 62, the second auxiliary transporting drive mechanism 46 drives and transports this rack 14 to the second receiving region 66 along the second auxiliary transporting path 36 (FIG. 10). When arrival of the rack 14 at the second receiving region 66 is detected based on an output signal of the second receiving region arrival sensor 74, the main transporting drive mechanism drives the rack 14 in the forward direction. When the second receiving region arrival sensor 74 outputs an ON signal, and subsequently, the second retraction sensor 78 outputs an ON signal and then outputs an OFF signal, it is detected that the rack 14 is retracted from the second receiving region 66 (FIG. 11). Feeding the rack 14 in the forward direction allows the second claw member 52 to come out from the receiving hole 48 of the rack, thereby allowing release of engagement of the rack 14 with the second claw member 52. When retraction of the rack 14 is detected, transporting drive by the main transporting drive device is stopped, and the second claw member 52 is directed to the start edge and moved to a region sandwiched between the end of the partition wall 28 and the sidewall 22 (FIG. 12). This position is a position which does not interfere with the rack 14 on the main transporting path 30 and the rack 14 on the second main transporting path 32, and therefore, it will be referred to as a retraction position, like in the above example. A position of the second claw member 52 can be known based on a rotation angle of the second auxiliary motor 56.

Figure 13:
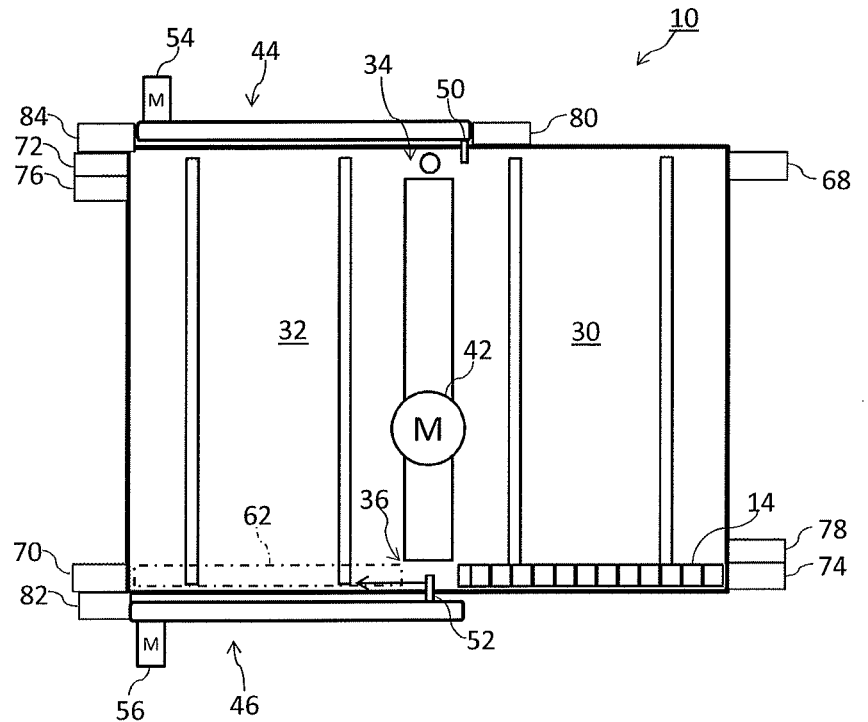
FIG. 13 shows an operation explanatory drawing of the rack transporting device 10 transporting one rack.
Figure 14:
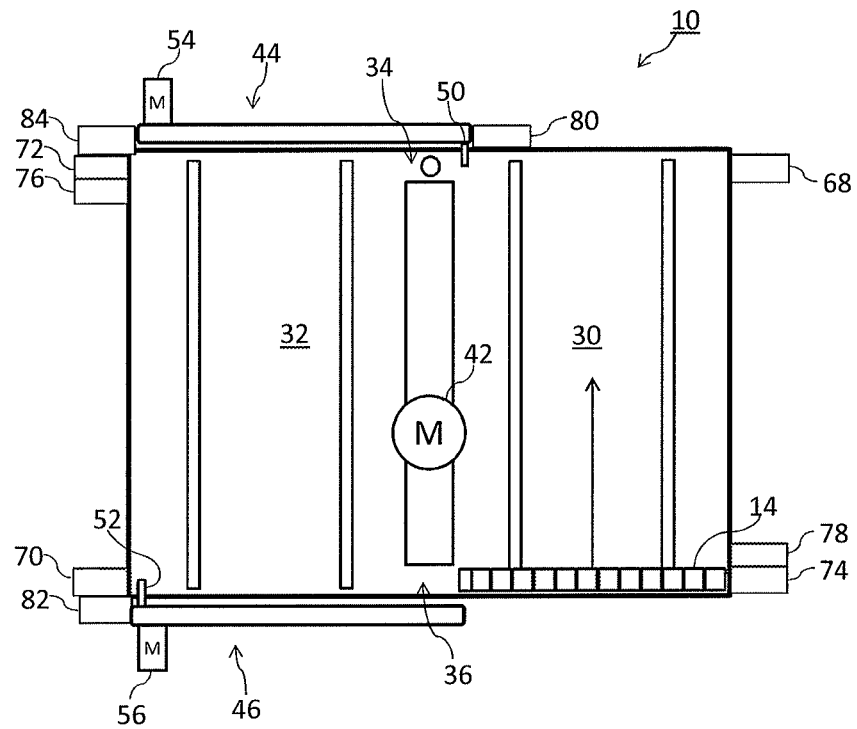
FIG. 14 shows an operation explanatory drawing of the rack transporting device 10 transporting one rack.

Next, the main transporting drive mechanism drives and transports the rack 14 in the reverse direction until arrival of the rack 14 at the second receiving region 66 is detected based on an output signal of the second receiving region arrival sensor 74 (FIG. 13). This operation by the main transporting drive mechanism also causes transporting drive to be performed on the second main transporting path 32 in the reverse direction, and this removes the rack 14 from the second end edge region 62. The second claw member 52 is moved to the start edge position, with no rack positioned in the second end edge region 62 (FIG. 14). Arrival of the second claw member 52 at the start edge position can be detected by the second start edge position sensor 82. By removing the possibility of the presence of the rack 14 in the second end edge region 62, the second claw member 52 is prevented from interfering with the rack 14 when the second claw member 52 is returned to the start edge position. Then, the main transporting drive mechanism drives and transports the rack 14 in the forward direction, and feeds it to the first end edge region 60. When the rack 14 arrives at the first end edge region 60, the operation returns to the state shown in FIG. 3.

In order to perform measurement a plurality of times for one sample, measurement is performed a plurality of times by repeating the operations described with reference to FIGS. 3 to 14.

Figure 15:
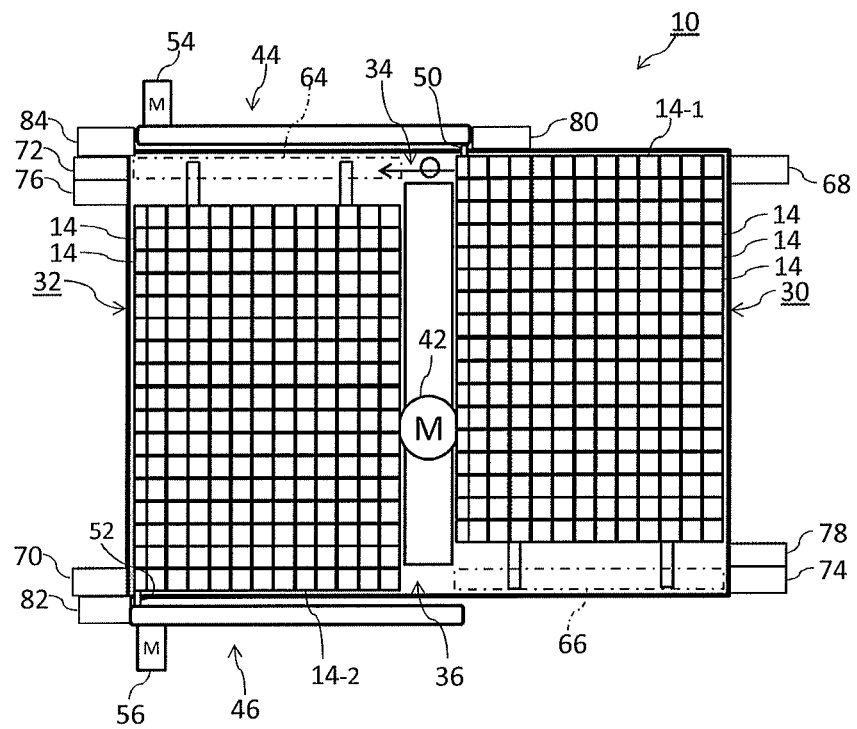
FIG. 15 shows an operation explanatory drawing of the rack transporting device 10 transporting a plurality of racks.

Further, operations of the rack transporting device 10 when a plurality of racks 14 are installed on the transporting table 12 will be described with reference to FIGS. 15 to 23. The shown example is an example where the table is fully loaded with the racks 14 (loaded with 34 racks). The operations begin with the state shown in FIG. 15. In order to obtain the state shown in FIG. 15, for example, 17 racks 14 are arranged on each of the first main transporting path 30 and the second main transporting path 32, and the main transporting drive mechanism is driven; that is, the main motor 42 is driven, to thereby drive and transport the racks 14 in the forward direction. Even if the lead rack reaches the end edge region on one main transporting path, transporting drive is continued, and transporting drive is performed until the lead racks reaches the end edge regions on both of the main transporting paths. Although a group of racks that arrive at the end edge region first are stopped by the sidewall, slippage is caused between the racks and the transporting belts, thereby allowing the transporting belts to be fed. When arrival of the racks 14 at the first end edge region 60 and the second end edge region 62 is detected based on output signals of the first end edge region arrival sensor 68 and the second end edge region arrival sensor 70, the state shown in FIG. 15 is reached. Even if the table is fully installed with the racks 14, it is possible to arrange no racks 14 in the regions to be detected by the first and the second receiving region arrival sensors 68 and 70 and the first and the second retraction sensors 76 and 78, as shown in FIG. 15. If an attempt is made to install the racks 14 in an overloaded manner, any one of the first and the second receiving region arrival sensors 68 and 70 and the first and the second retraction sensors 76 and 78 detects those racks 14, and reports an overload error based on this.

Figure 16:
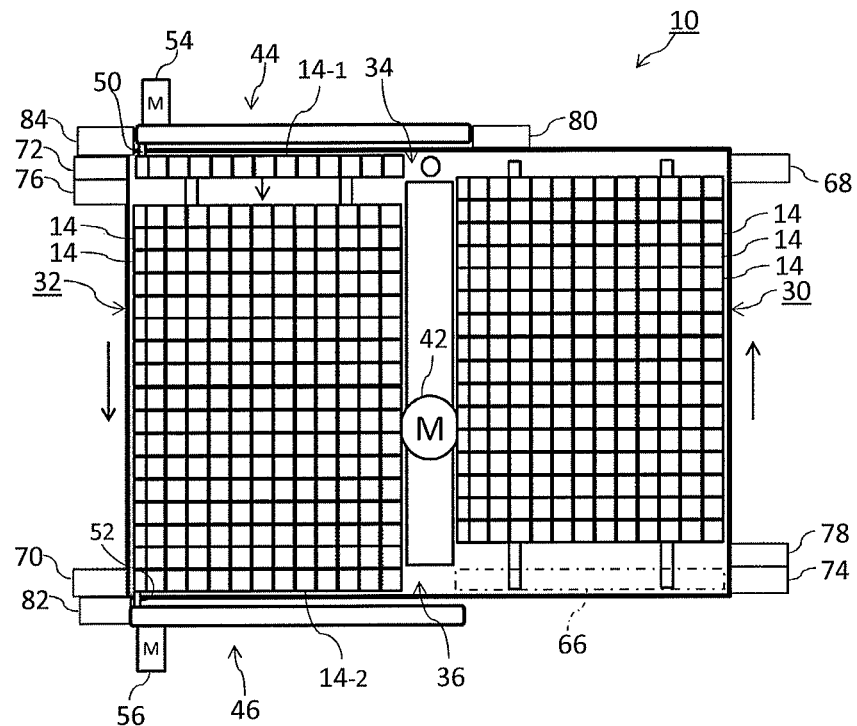
FIG. 16 shows an operation explanatory drawing of the rack transporting device 10 transporting a plurality of racks.

First, the first auxiliary transporting drive mechanism 44 drives and transports the lead rack 14-1 on the first main transporting path 30 in the forward direction. When the rack 14-1 is transported, and the lead container 16 reaches the position of the measurement section entrance 58, the rack 14-1 is stopped, and the container 16 is fed to the measurement section. After the measurement is finished, the container 16 is returned to its original position in the rack 14-1, and the rack 14 is transported until a next container 16 reaches the position of the measurement section entrance 58. This is repeated for each container 16, and after the measurement is finished for all of the containers 16 on this rack 14-1, the rack 14-1 is transported to the first receiving region 64 of the second main transporting path 32 (FIG. 16).

Feeding of the rack 14 can be controlled based on a rotation angle of the first auxiliary motor 54.

Figure 17:
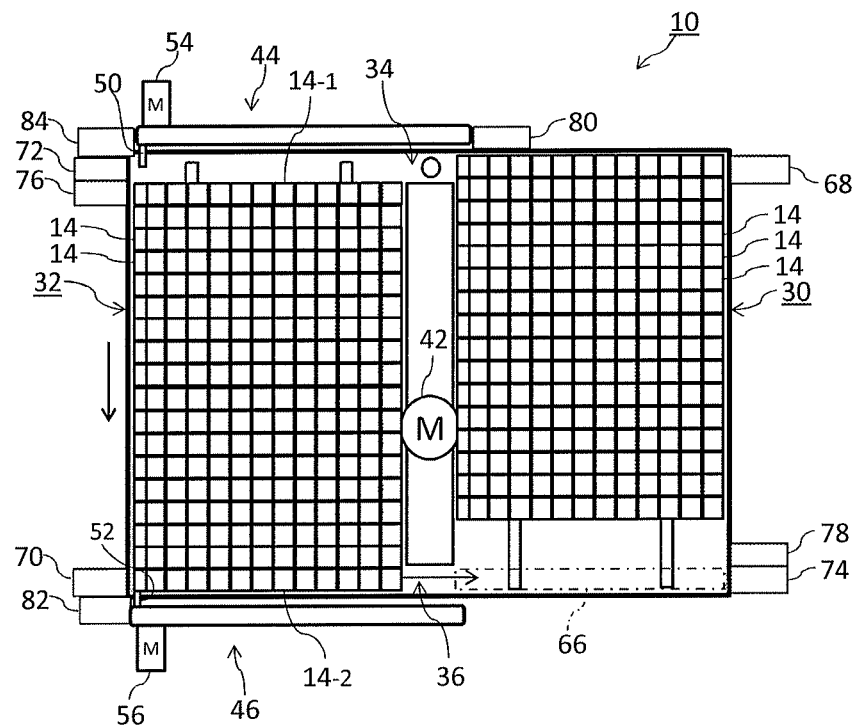
FIG. 17 shows an operation explanatory drawing of the rack transporting device 10 transporting a plurality of racks.
Figure 18:
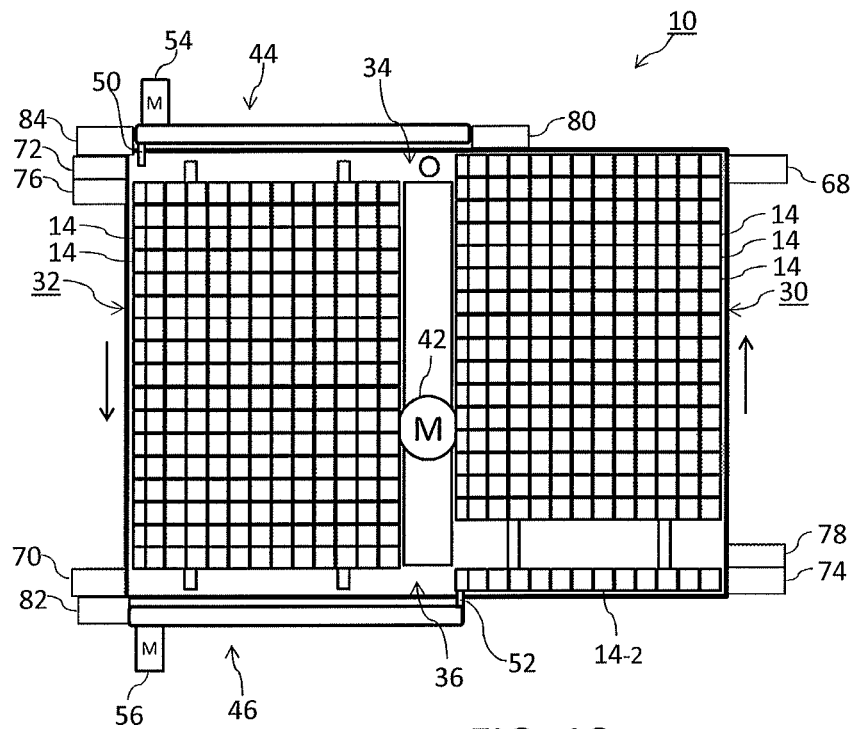
FIG. 18 shows an operation explanatory drawing of the rack transporting device 10 transporting a plurality of racks.

When arrival of the rack 14-1 at the first receiving region 64 is detected based on an output signal of the first receiving region arrival sensor 72, the main transporting drive mechanism drives and transports the rack 14-1 in the forward direction. Although the other racks 14 on the second main transporting path 32 abut against the sidewall 22 and thus cannot move forward any further, the transporting belts 40 can slip with respect to these racks 14 and move, thereby driving and transporting the rack 14-1. This transporting drive in the forward direction also causes the racks 14 on the first main transporting path 30 to be driven and transported (FIG. 17). When arrival of the rack 14 at the first end edge region 60 is detected based on an output signal of the first end edge region arrival sensor 68, the main transporting drive mechanism is temporarily suspended, and the second auxiliary transporting drive mechanism 46 feeds the rack 14-2 to the second receiving region 66 (FIG. 18).

Figure 19:
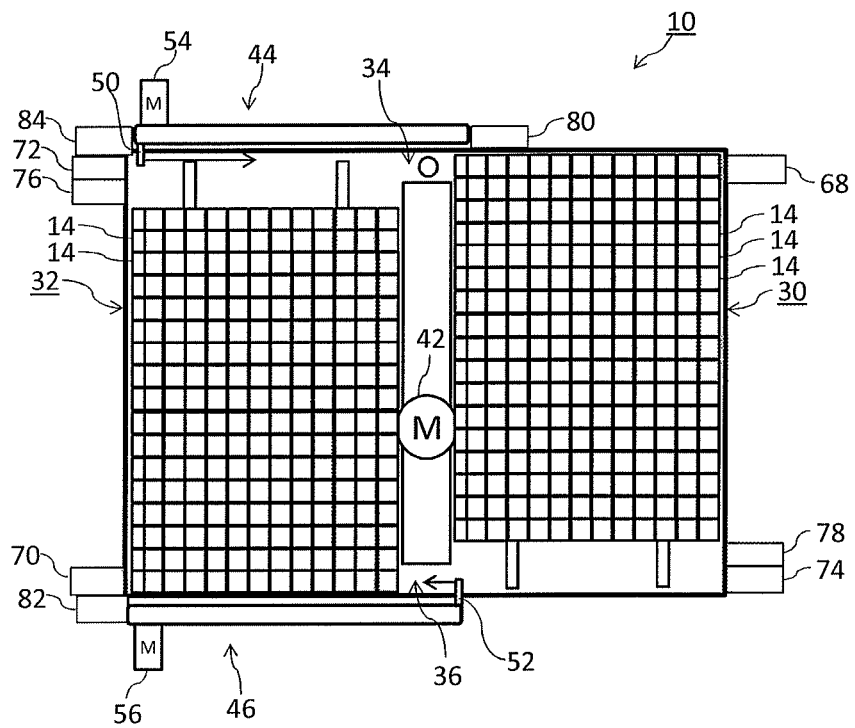
FIG. 19 shows an operation explanatory drawing of the rack transporting device 10 transporting a plurality of racks.
Figure 20:
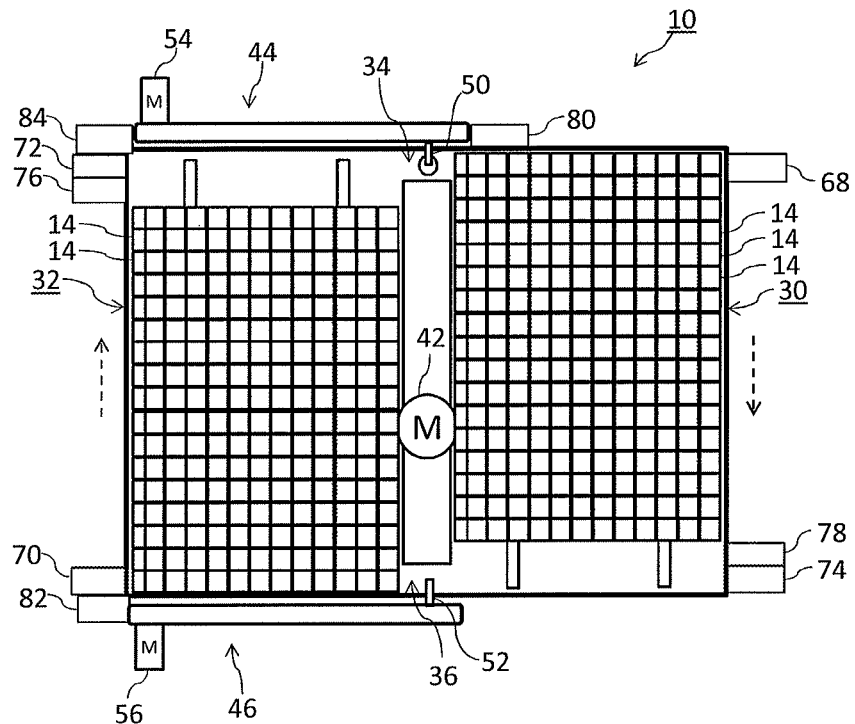
FIG. 20 shows an operation explanatory drawing of the rack transporting device 10 transporting a plurality of racks.

When arrival of the rack 14-2 at the second receiving region 66 is detected based on an output signal of the second receiving region arrival sensor 74, the main transporting drive mechanism drives and transports the racks 14 in the forward direction. When the first receiving region arrival sensor 72 outputs an ON signal, and subsequently, the first retraction sensor 76 outputs an ON signal and then an OFF signal, it is detected that the rack 14-1 is retracted from the first receiving region 64. In addition, when the second receiving region arrival sensor 74 outputs an ON signal, and subsequently, the second retraction sensor 78 outputs an ON signal and then outputs an OFF signal, it is detected that the rack 14-2 is retracted from the second receiving region 66 (FIG. 19). This allows the first claw member 50 to come out from the receiving hole 48 of the rack 14-1, thereby allowing release of engagement between them. The second claw member 52 is also allowed to come out from the receiving hole 48 of the rack 14-2, thereby allowing release of engagement between them. When retraction of the racks 14-1 and 14-2 is detected, the main transporting drive mechanism is stopped, and the first claw member 50 is directed to its start end and moved to the retraction position. Similarly, the second claw member 52 is directed to its start edge and moved to the retraction position (FIG. 20). A position of the first claw member 50 can be known based on a rotation angle of the first auxiliary motor 54. A position of the second claw member 52 can be known based on a rotation angle of the second auxiliary motor 56.

Figure 21:
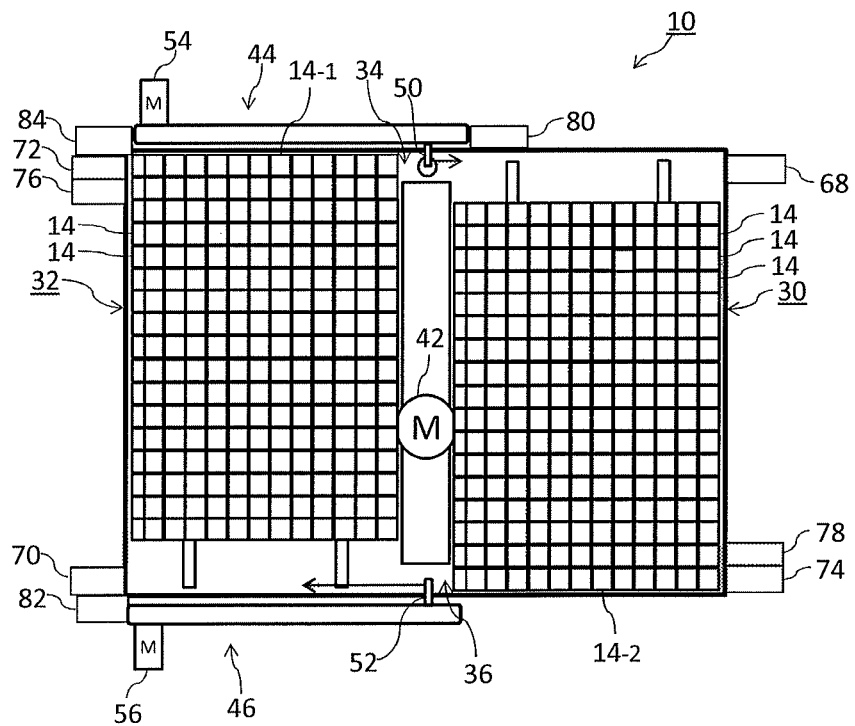
FIG. 21 shows an operation explanatory drawing of the rack transporting device 10 transporting a plurality of racks.
Figure 22:
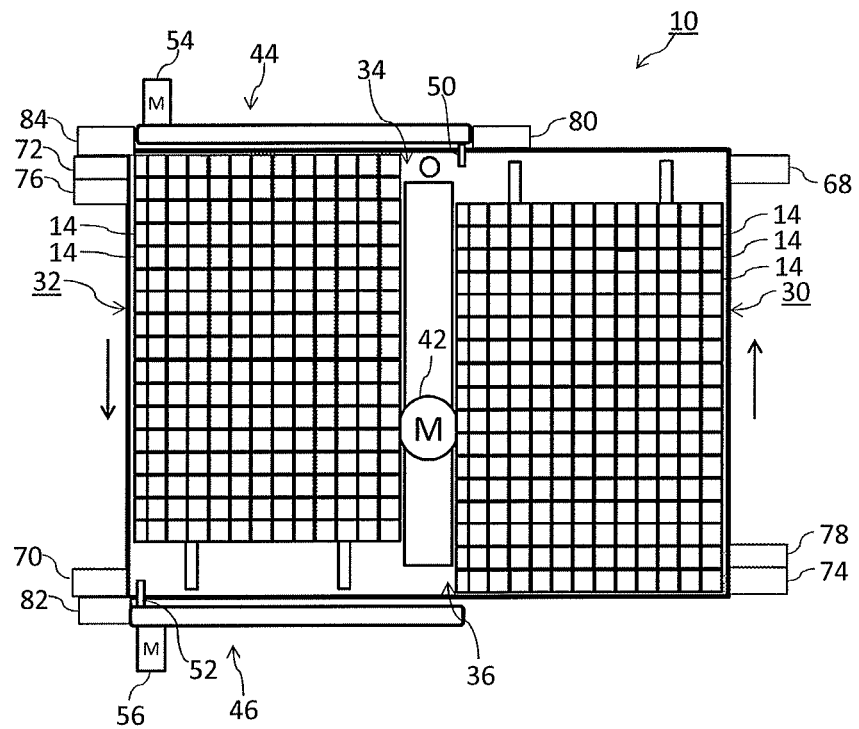
FIG. 22 shows an operation explanatory drawing of the rack transporting device 10 transporting a plurality of racks.
Figure 23:
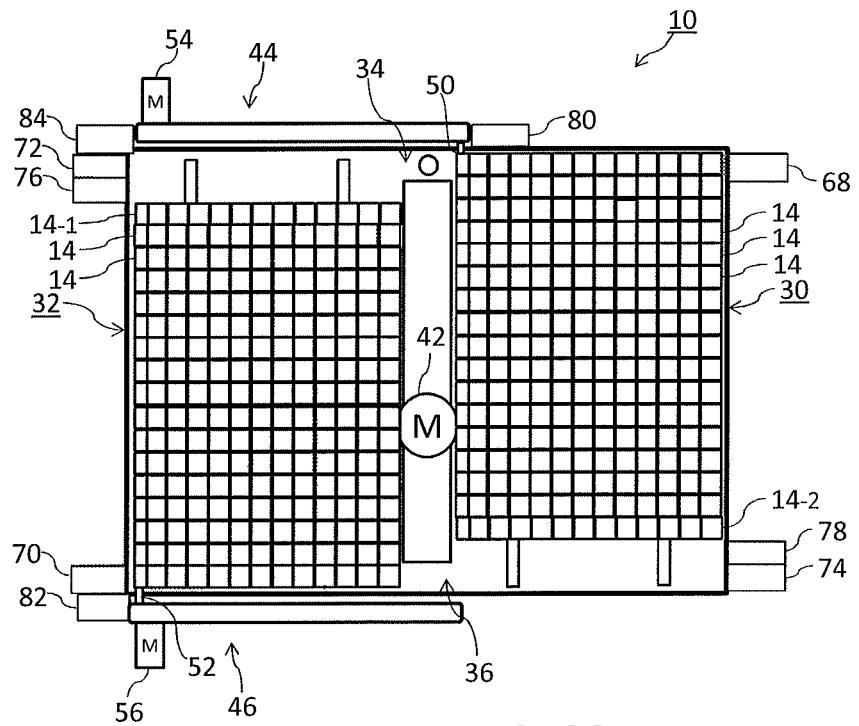
FIG. 23 shows an operation explanatory drawing of the rack transporting device 10 transporting a plurality of racks.

Next, the main transporting drive mechanism drives and transports the racks 14 in the reverse direction until the rack 14-1 is detected by the first receiving region arrival sensor 72 and the rack 14-2 is detected by the second receiving region arrival sensor 74 (FIG. 21). This operation by the main transporting drive mechanism removes the racks 14 from the first and the second end edge regions 60 and 62. The first and the second claw members 50 and 52 are moved to the start edge positions, with no rack positioned in the first and the second end edge regions 60 and 62 (FIG. 22). Arrival of the first and the second claw members 50 and 52 at the start edge positions can be detected by the first and the second start edge position sensors 80 and 82, respectively. By removing the possibility of the presence of the racks 14 in the first and the second end edge regions 60 and 62 by transporting the racks 14 in the reverse direction, the first and the second claw members 50 and 52 are prevented from interfering with the racks 14 when they are returned to the start edge positions. Then, the main transporting drive mechanism drives and transports the racks 14 in the forward direction, and feeds them to the first and the second end edge regions 60 and 62. The racks 14 fed to the first and the second end edge regions 60 and 62 are respectively engaged with the first and the second claw members 50 and 52 through their receiving holes 48 (FIG. 23). The state shown in FIG. 23 is obtained by feeding the racks 14 by one rack from the state shown in FIG. 15. Subsequently, the samples in the containers 16 are measured by repeating the operations in FIGS. 15 to 23 and causing the racks 14 to circulate once or more times.

In the above-described example where the plurality of racks 14 are processed, after the rack 14-1 arrives at the first receiving region 64, the main transporting drive mechanism once performs transporting drive in the forward direction, and then the rack 14-2 is fed to the second receiving region 66. Alternatively, after the rack 14-1 arrives at the first receiving region 64, the rack 14-2 may first be fed to the second receiving region 66, and then the main transporting drive mechanism may perform transporting drive in the forward direction.

Figure 24:
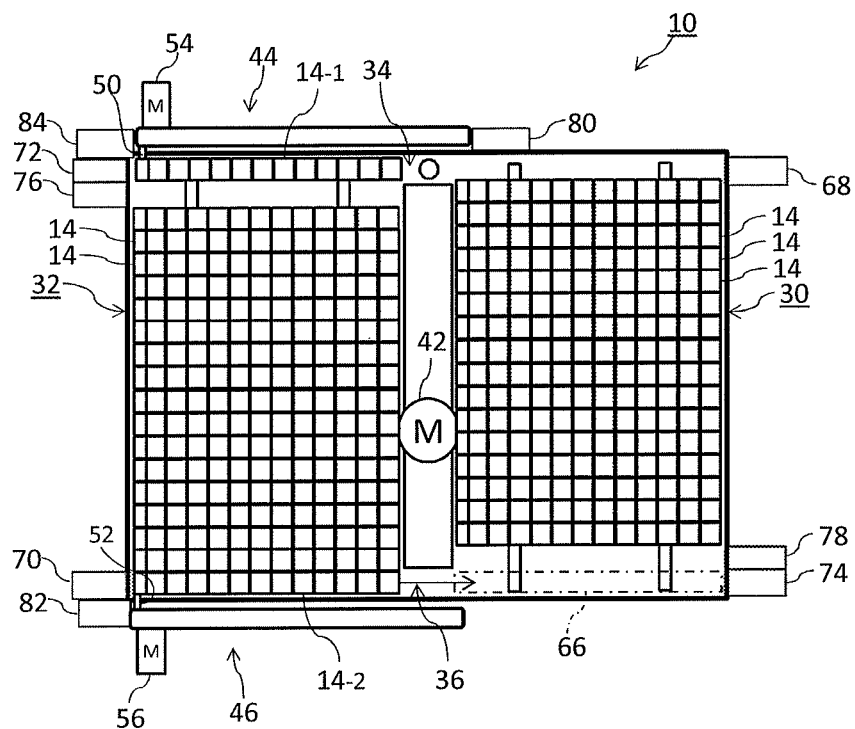
FIG. 24 shows an operation explanatory drawing of the rack transporting device 10 transporting a plurality of racks.
Figure 25:
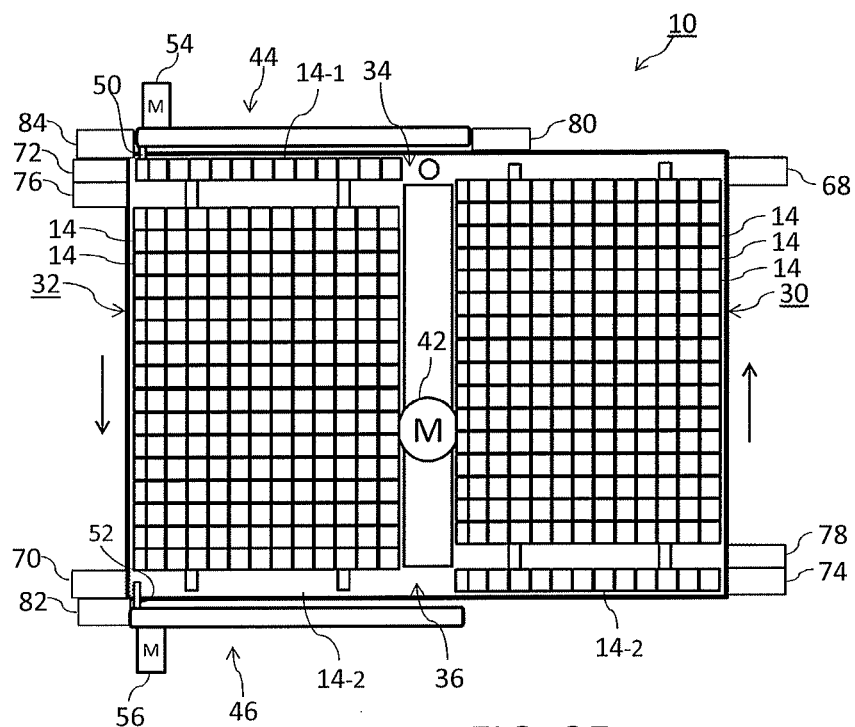
FIG. 25 shows an operation explanatory drawing of the rack transporting device 10 transporting a plurality of racks.

A detailed description will be provided. The first auxiliary transporting drive mechanism 44 drives and transports the lead rack 14-1 on the first main transporting path 30 in the forward direction from the state shown in FIG. 15. Like in the above-described example, after the measurement is finished for all of the containers 16 held in the rack 14-1, the rack 14-1 is fed to the first receiving region 64 on the second main transporting path 32 (FIG. 24). When arrival of the rack 14-1 at the first receiving region 64 is detected based on an output signal of the first receiving region arrival sensor 72, the second auxiliary transporting drive mechanism 46 feeds the rack 14-2 to the second receiving region 66 (FIG. 25). When arrival of the rack 14-2 at the second receiving region 66 is detected based on an output signal of the second receiving region arrival sensor 74, the main transporting drive mechanism drives and transports the racks 14 in the forward direction. When the first receiving region arrival sensor 72 outputs an ON signal, and subsequently, the first retraction sensor 76 outputs an ON signal and then an OFF signal, it is detected that the rack 14-1 is retracted from the first receiving region 64. In addition, when the second receiving region arrival sensor 74 outputs an ON signal, and subsequently, the second retraction sensor 78 outputs an ON signal and then outputs an OFF signal, it is detected that the rack 14-2 is retracted from the second receiving region 66. This is the state shown in FIG. 19. The subsequent operations are the same as those described with reference to FIGS. 19 to 23.

Further, the second transporting drive mechanism 46 can also drive and transport the rack 14-2 while the first auxiliary transporting drive mechanism 44 drives and transports the rack 14-1. In this case, when both of the first and the second receiving region arrival sensors 72 and 74 output ON signals, it is detected that the state shown in FIG. 25 is obtained, and the main transporting drive mechanism performs transporting drive in the forward direction. The subsequent operations are the same as those described with reference to FIGS. 19 to 24.

REFERENCE SIGNS LIST 10 rack transporting device, 12 transporting table, 14 rack, 30 first main transporting path, 32 second main transporting path, 34 first auxiliary transporting path, 36 second auxiliary transporting path, 38, 40 transporting belts, 42 main motor, 44 first auxiliary transporting drive mechanism, 46 second auxiliary transporting drive mechanism, 48 receiving hole, 50 first claw member, 52 second claw member, 54 first auxiliary motor, 55 second auxiliary motor, 60 first end edge region, 62 second end edge region, 64 first receiving region, 66 second receiving region, 68 first end edge region arrival sensor, 70 second end edge region arrival sensor, 72 first receiving region arrival sensor, 74 second receiving region arrival sensor, 76 first retraction sensor, 78 second retraction sensor.

The invention claimed is:

1. A rack transporting device for transporting at least one rack holding a plurality of containers, the device comprising:
  a first main transporting path through which the rack is transported in a short-side direction of the rack;
  a second main transporting path which extends parallel to the first main transporting path and through which the rack is transported in the short-side direction of the rack;
  a first auxiliary transporting path which extends in a direction orthogonal to the first main transporting path and the second main transporting path and connects between an end of the first main transporting path and an end of the second main transporting path, and through which the rack is transported in a longitudinal direction of the rack;
  a main transporting drive mechanism which simultaneously drives and transports the rack on the first main transporting path and the rack on the second main transporting path in a forward direction along which the racks are transported from the first main transporting path to the second main transporting path through the first auxiliary transporting path, the main transporting drive mechanism also simultaneously driving and transporting the rack on the first main transporting path and the rack on the second main transporting path in a reverse direction that is opposite to the forward direction;
  a first auxiliary transporting drive mechanism which drives and transports the rack on the first auxiliary transporting path, the first auxiliary transporting drive mechanism having a first claw member to be engaged with a receiving hole formed in a side surface of the rack along the longitudinal direction of the rack, the first auxiliary transporting drive mechanism feeding the first claw member engaged with the receiving hole, thereby driving and transporting the rack on the first auxiliary transporting path;
  a first end edge region arrival detector which detects that the rack arrives at a first end edge region, the first end edge region being an end edge of the first main transporting path for transport in the forward direction;
  a first receiving region arrival detector which detects that the rack arrives at a first receiving region on the second main transporting path, the first receiving region receiving the rack transported through the first auxiliary transporting path; and
  a first retraction detector which detects that the rack is retracted from the first receiving region, wherein:
  the first auxiliary transporting drive mechanism drives and transports the rack from the first end edge region toward the first receiving region;
  when the first receiving region arrival detector detects arrival of the rack at the first receiving region, the main transporting drive mechanism drives and transports the rack in the forward direction;
  when the first retraction detector detects retraction of the rack from the first receiving region, the first auxiliary transporting drive mechanism moves the first claw member to a retraction position which does not interfere with the rack on the first main transporting path and the rack on the second main transporting path;
  after the first claw member is moved to the retraction position, the main transporting drive mechanism drives and transports the rack in the reverse direction;
  when the first receiving region arrival detector detects that the rack is returned and arrives at the first receiving region, the first auxiliary transporting drive mechanism moves the first claw member to a start edge position at which the first claw member is engageable with a rack transported to the end edge region;
  after the first claw member is moved to the start edge position, the main transporting drive mechanism drives and transports the rack in the forward direction, thereby engaging the receiving hole of the rack with the first claw member; and
  when the first end edge region arrival detector detects arrival of the rack at the first end edge region, the main transporting drive mechanism is stopped, and the first auxiliary transporting drive mechanism drives and transports the rack from the first end edge region toward the first receiving region.

2. The rack transporting device according to claim 1, further comprising:
  a second auxiliary transporting path which extends in a direction orthogonal to the first main transporting path and the second main transporting path and connects between ends of the first main transporting path and the second main transporting path on the side opposite to the side where the first auxiliary transporting path is located, and through which the rack is transported in the longitudinal direction of the rack;
  a second auxiliary transporting drive mechanism which drives and transports a rack on the second auxiliary transporting path, the second auxiliary transporting drive mechanism having a second claw member to be engaged with a receiving hole formed in a side surface of the rack along the longitudinal direction of the rack, the second auxiliary transporting drive mechanism feeding the second claw member engaged with the receiving hole, thereby driving and transporting the rack on the second auxiliary transporting path;
  a second end edge region arrival detector which detects that the rack arrives at a second end edge region, the second end edge region being an end edge of the second main transporting path for transport in the forward direction;
  a second receiving region arrival detector which detects that the rack arrives at a second receiving region on the first main transporting path, the second receiving region receiving the rack transported through the second auxiliary transporting path; and
  a second retraction detector which detects that the rack is retracted from the second receiving region, wherein:
  the first auxiliary transporting drive mechanism drives and transports the rack from the first end edge region toward the first receiving region;
  when the first receiving region arrival detector detects arrival of the rack at the first receiving region, the main transporting drive mechanism drives and transports the rack in the forward direction;
  when the first end edge region arrival detector detects arrival of the rack at the first end edge region, the second auxiliary transporting drive mechanism drives and transports a rack from the second end edge region toward the second receiving region;

when the second receiving region arrival detector detects arrival of the rack at the second receiving region, the main transporting drive mechanism drives and transports the rack in the forward direction;

when the first retraction detector detects retraction of the rack from the first receiving region, and when the second retraction detector detects retraction of the rack from the second receiving region, the first auxiliary transporting drive mechanism and the second auxiliary transporting drive mechanism respectively move the first claw member and the second claw member to retraction positions which do not interfere with the rack on the first main transporting path and the rack on the second main transporting path, respectively;

after the first claw member and the second claw member are moved to the retraction positions, the main transporting drive mechanism drives and transports the racks in the reverse direction;

when the first receiving region arrival detector detects that the rack is returned and arrives at the first receiving region, and when the second receiving region arrival detector detects that the rack is returned and arrives at the second receiving region, the first auxiliary transporting drive mechanism moves the first claw member to the start edge position at which the first claw member is engageable with a rack transported to the first end edge region, and the second auxiliary transporting drive mechanism moves the second claw member to a start edge position at which the second claw member is engageable with a rack transported to the second end edge region;

after the first claw member and the second claw member are moved to the respective start edge positions, the main transporting drive mechanism drives and transports the racks in the forward direction, thereby engaging the receiving hole of the rack on the first main transporting path with the first claw member and engaging the receiving hole of the rack on the second main transporting path with the second claw member; and when the first end edge region arrival detector detects arrival of the rack at the first end edge region, and when the second end edge region arrival detector detects arrival of the rack at the second end edge region, the main transporting drive mechanism is stopped, and the first auxiliary transporting drive mechanism drives and transports the rack from the first end edge region toward the first receiving region.

3. The rack transporting device according to claim 1, further comprising:

a second auxiliary transporting path which extends in a direction orthogonal to the first main transporting path and the second main transporting path and connects between ends of the first main transporting path and the second main transporting path on the side opposite to the side where the first auxiliary transporting path is located, and through which the rack is transported in the longitudinal direction of the rack;

a second auxiliary transporting drive mechanism which drives and transports a rack on the second auxiliary transporting path, the second auxiliary transporting drive mechanism having a second claw member to be engaged with a receiving hole formed in a side surface of the rack along the longitudinal direction of the rack, the second auxiliary transporting drive mechanism feeding the second claw member engaged with the receiving hole, thereby driving and transporting the rack on the second auxiliary transporting path;

a second end edge region arrival detector which detects that the rack arrives at a second end edge region, the second end edge region being an end edge of the second main transporting path for transport in the forward direction;

a second receiving region arrival detector which detects that the rack arrives at a second receiving region on the first main transporting path, the second receiving region receiving the rack transported through the second auxiliary transporting path; and a second retraction detector which detects that the rack is retracted from the second receiving region, wherein:

the first auxiliary transporting drive mechanism drives and transports the rack from the first end edge region toward the first receiving region;

while the first auxiliary transporting drive mechanism performs transporting drive or when the first receiving region arrival detector detects arrival of the rack at the first receiving region, the second auxiliary transporting drive mechanism drives and transports a rack from the second end edge region toward the second receiving region;

when the first receiving region arrival detector detects arrival of the rack at the first receiving region and when the second receiving region arrival detector detects arrival of the rack at the second receiving region, the main transporting drive mechanism drives and transports the racks in the forward direction;

when the first retraction detector detects retraction of the rack from the first receiving region, and when the second retraction detector detects retraction of the rack from the second receiving region, the first auxiliary transporting drive mechanism and the second auxiliary transporting drive mechanism respectively move the first claw member and the second claw member to retraction positions which do not interfere with the rack on the first main transporting path and the rack on the second main transporting path, respectively;

after the first claw member and the second claw member are moved to the retraction positions, the main transporting drive mechanism drives and transports the racks in the reverse direction;

when the first receiving region arrival detector detects that the rack is returned and arrives at the first receiving region, and when the second receiving region arrival detector detects that the rack is returned and arrives at the second receiving region, the first auxiliary transporting drive mechanism moves the first claw member to the start edge position at which the first claw member is engageable with a rack transported to the first end edge region, and the second auxiliary transporting drive mechanism moves the second claw member to a start edge position at which the second claw member is engageable with a rack transported to the second end edge region;

after the first claw member and the second claw member are moved to the respective start edge positions, the main transporting drive mechanism drives and transports the racks in the forward direction, thereby engaging the receiving hole of the rack on the first main transporting path with the first claw member and engaging the receiving hole of the rack on the second main transporting path with the second claw member; and when the first end edge region arrival detector detects arrival of the rack at the first end edge region, and when the second end edge region arrival detector detects arrival of the rack at the second end edge region, the main transporting drive mechanism is stopped, and the first auxiliary transporting drive mechanism drives and transports the rack from the first end edge region toward the first receiving region.

4. A method for transporting a rack in at least one rack transporting device, the rack transporting device comprising:
   a first main transporting path through which the rack is transported in a short-side direction of the rack;
   a second main transporting path which extends parallel to the first main transporting path and through which the rack is transported in the short-side direction of the rack;
   a first auxiliary transporting path which extends in a direction orthogonal to the first main transporting path and the second main transporting path and connects between an end of the first main transporting path and an end of the second main transporting path, and through which the rack is transported in a longitudinal direction of the rack;
   a main transporting drive mechanism which simultaneously drives and transports the rack on the first main transporting path and the rack on the second main transporting path in a forward direction along which the racks are transported from the first main transporting path to the second main transporting path through the first auxiliary transporting path, the main transporting drive mechanism also simultaneously driving and transporting the rack on the first main transporting path and the rack on the second main transporting path in a reverse direction that is opposite to the forward direction; and
   a first auxiliary transporting drive mechanism which drives and transports the rack on the first auxiliary transporting path, the first auxiliary transporting drive mechanism having a first claw member to be engaged with a receiving hole formed in a side surface of the rack along the longitudinal direction of the rack, the first auxiliary transporting drive mechanism feeding the first claw member engaged with the receiving hole, thereby driving and transporting the rack on the first auxiliary transporting path, wherein the method comprises the steps of:
   driving and transporting the rack from a first end edge region toward a first receiving region on the second main transporting path by the first auxiliary transporting drive mechanism, the first end edge region being an end edge of the first main transporting path for transport in the forward direction, the first receiving region receiving the rack transported through the first auxiliary transporting path;
   when the rack arrives at the first receiving region, driving and transporting the rack in the forward direction by the main transporting drive mechanism;
   when the rack is retracted from the first receiving region, moving the first claw member to a retraction position by the first auxiliary transporting drive mechanism, the retraction position not interfering with the rack on the first main transporting path and the rack on the second main transporting path;
   after the first claw member is moved to the retraction position, driving and transporting the main rack in the reverse direction by the transporting drive mechanism;
   when the rack is returned and arrives at the first receiving region, moving the first claw member to a start edge position by the first auxiliary transporting drive mechanism, the first claw member being engageable with a rack transported to the first end edge region at the start edge position;
   after the first claw member is moved to the start edge position, driving and transporting the rack in the forward direction by the main transporting drive mechanism, thereby engaging the receiving hole of the rack with the first claw member; and
   when the rack arrives at the first end edge region, stopping the main transporting drive mechanism and driving and transporting the rack from the first end edge region toward the first receiving region by the first auxiliary transporting drive mechanism.

5. The method according to claim 4, wherein the rack transporting device further comprises:
   a second auxiliary transporting path which extends in a direction orthogonal to the first main transporting path and the second main transporting path and connects between ends of the first main transporting path and the second main transporting path on the side opposite to the side where the first auxiliary transporting path is located, and through which the rack is transported in the longitudinal direction of the rack; and
   a second auxiliary transporting drive mechanism which drives and transports the rack on the second auxiliary transporting path, the second auxiliary transporting drive mechanism having a second claw member to be engaged with a receiving hole formed in a side surface of the rack along the longitudinal direction of the rack, the second auxiliary transporting drive mechanism feeding the second claw member engaged with the receiving hole, thereby driving and transporting the rack on the second auxiliary transporting path, wherein the method further comprises the steps of:
   driving and transporting the rack from the first end edge region toward the first receiving region by the first auxiliary transporting drive mechanism;
   when the rack arrives at the first receiving region, driving and transporting the rack in the forward direction by the main transporting drive mechanism;
   when the rack arrives at the first end edge region, driving and transporting a rack from a second end edge region toward a second receiving region on the first main transporting path by the second auxiliary transporting drive mechanism, the second end edge region being an end edge of the second main transporting path for transport in the forward direction, the second receiving region receiving the rack transported through the second auxiliary transporting path;
   when the rack arrives at the second receiving region, driving and transporting the rack in the forward direction by the main transporting drive mechanism;
   when the rack is retracted from the first receiving region, and when the rack is retracted from the second receiving region, moving the first claw member and the second claw member to respective retraction positions by the first auxiliary transporting drive mechanism and the second auxiliary transporting drive mechanism, respectively, the retraction positions not interfering with the rack on the first main transporting path and the rack on the second main transporting path, respectively;
   after the first claw member and the second claw member are moved to the retraction positions, driving and transporting the racks in the reverse direction by the main transporting drive mechanism;

when the rack is returned and arrives at the first receiving region, and when the rack is returned and arrives at the second receiving region, moving the first claw member to a start edge position by the first auxiliary transporting drive mechanism, and moving the second claw member to a start edge position by the second auxiliary transporting drive mechanism, the first claw member being engageable with a rack transported to the first end edge region at the start edge position, the second claw member being engageable with a rack transported to the second end edge region at the start edge position;

after the first claw member and the second claw member are moved to the respective start edge positions, driving and transporting the racks in the forward direction by the main transporting drive mechanism, thereby engaging the receiving hole of the rack on the first main transporting path with the first claw member and engaging the receiving hole of the rack on the second main transporting path with the second claw member; and when the rack arrives at the first end edge region, and when the rack arrives at the second end edge region, stopping the main transporting drive mechanism and driving and transporting the rack from the first end edge region toward the first receiving region by the first auxiliary transporting drive mechanism.

6. The method according to claim 4, wherein the rack transporting device further comprises:

a second auxiliary transporting path which extends in a direction orthogonal to the first main transporting path and the second main transporting path and connects between ends of the first main transporting path and the second main transporting path on the side opposite to the side where the first auxiliary transporting path is located, and through which the rack is transported in the longitudinal direction of the rack; and a second auxiliary transporting drive mechanism which drives and transports a rack on the second auxiliary transporting path, the second auxiliary transporting drive mechanism having a second claw member to be engaged with a receiving hole formed in a side surface of the rack along the longitudinal direction of the rack, the second auxiliary transporting drive mechanism feeding the second claw member engaged with the receiving hole, thereby driving and transporting the rack on the second auxiliary transporting path, wherein the method further comprises the steps of:

driving and transporting the rack from the first end edge region toward the first receiving region by the first auxiliary transporting drive mechanism;

while the first auxiliary transporting drive mechanism performs transporting drive or when the rack arrives at the first end edge region, driving and transporting a rack from a second end edge region toward a second receiving region on the first main transporting path by the second auxiliary transporting drive mechanism, the second end edge region being an end edge of the second main transporting path for transport in the forward direction, the second receiving region receiving the rack transported through the second auxiliary transporting path;

when the rack arrives at the first receiving region, and when the rack arrives at the second receiving region, driving and transporting the racks in the forward direction by the main transporting drive mechanism;

when the rack is retracted from the first receiving region, and when the rack is retracted from the second receiving region, moving the first claw member and the second claw member to respective retraction positions by the first auxiliary transporting drive mechanism and the second auxiliary transporting drive mechanism, respectively, the retraction positions not interfering with the rack on the first main transporting path and the rack on the second main transporting path, respectively;

after the first claw member and the second claw member are moved to the retraction positions, driving and transporting the racks in the reverse direction by the main transporting drive mechanism;

when the rack is returned and arrives at the first receiving region, and when the rack is returned and arrives at the second receiving region, moving the first claw member to a start edge position by the first auxiliary transporting drive mechanism, and moving the second claw member to a start edge position by the second auxiliary transporting drive mechanism, the first claw member being engageable with a rack transported to the first end edge region at the start edge position, and the second claw member being engageable with a rack transported to the second end edge region at the start edge position;

after the first claw member and the second claw member are moved to the respective start edge positions, driving and transporting the racks in the forward direction by the main transporting drive mechanism, thereby engaging the receiving hole of the rack on the first main transporting path with the first claw member and engaging the receiving hole of the rack on the second main transporting path with the second claw member; and when the rack arrives at the first end edge region, and when the rack arrives at the second end edge region, stopping the main transporting drive mechanism, and driving and transporting the rack from the first end edge region toward the first receiving region by the first auxiliary transporting drive mechanism.

* * * * *